US012760090B2

(12) United States Patent
Hong et al.

(10) Patent No.: US 12,760,090 B2
(45) Date of Patent: Oct. 13, 2026

(54) COMBINATION THERAPY

(71) Applicant: ViiV Healthcare Company, Wilmington, DE (US)

(72) Inventors: Zhi Hong, Research Triangle Park, NC (US); Jerry Lee Jeffrey, Research Triangle Park, NC (US); Brian Alvin Johns, Research Triangle Park, NC (US); Andrew Spaltenstein, Raleigh, NC (US); Emile Johann Velthuisen, Research Triangle Park, NC (US)

(73) Assignee: ViiV Healthcare Company, Wilmington, DE (US)

( * ) Notice: Subject to any disclaimer, the term of this patent is extended or adjusted under 35 U.S.C. 154(b) by 643 days.

(21) Appl. No.: 18/255,920

(22) PCT Filed: Dec. 3, 2021

(86) PCT No.: PCT/US2021/061697
§ 371 (c)(1),
(2) Date: Jun. 5, 2023

(87) PCT Pub. No.: WO2022/125378
PCT Pub. Date: Jun. 16, 2022

(65) Prior Publication Data

US 2025/0296988 A1 Sep. 25, 2025

Related U.S. Application Data

(60) Provisional application No. 63/122,031, filed on Dec. 7, 2020.

(51) Int. Cl.
*C07K 16/114* (2026.01)
*A61K 31/4985* (2006.01)
*A61K 39/00* (2006.01)
*A61P 31/18* (2006.01)

(52) U.S. Cl.
CPC ...... *C07K 16/1145* (2026.01); *A61K 31/4985* (2013.01); *A61P 31/18* (2018.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 10,562,960 | B2 * | 2/2020 | Connors | C07K 16/1063 |
| 2016/0347816 | A1 * | 12/2016 | Toporik | A61P 11/00 |
| 2018/0371086 | A1 | 12/2018 | Cihlar et al. | |
| 2019/0328900 | A1 | 10/2019 | Jeffrey et al. | |
| 2020/0138845 | A1 | 5/2020 | Scott | |
| 2020/0223907 | A1 * | 7/2020 | Balakrishnan | A61P 31/18 |
| 2020/0368347 | A1 | 11/2020 | Moldt et al. | |

FOREIGN PATENT DOCUMENTS

| | | | |
|---|---|---|---|
| JP | 2020527570 | A | 9/2020 |
| JP | 2021529530 | A | 11/2021 |
| WO | WO 2016/154003 | | 9/2016 |
| WO | WO2017/205585 | | 11/2017 |
| WO | WO2021/116872 | | 6/2021 |

OTHER PUBLICATIONS

Rudikoff, et al., Proceedings of the National Academy of Sciences, National Academy of Sciences, vol. 79, Mar. 1, 1982, pp. 1979-1983.

Gsk: "Meet Gsk Management Getting ahead of HIV", Nov. 29, 2021 (Nov. 29, 2021), XP55898996, Retrieved from the Internet:URL:https://www.gsk.com/media/7290/gsk_getting_ahead_of_hiv-evnt-presentation-29-nov-21.pdf [retrieved on Mar. 8, 2022] p. 24.

Anonymous: "History of Changes for Study: NCT03739996 Long-Acting Cabotegravir Plus VRC-HIVMAB075-00-AB (VRC07-523LS) for Viral Suppression in Adults Living With HIV-1", Clinical Trails, Mar. 22, 2023, XP093271840, 9 Pages.

Baum M.M., et al., "Highly Synergistic Drug Combination Prevents Vaginal HIV Infection in Humanized Mice," Scientific Reports, vol. 10(1), Aug. 3, 2020, XP09327184, pp. 1-9.

International Search Report and Written Opinion for International Application No. PCT/US2021/061697, mailed Mar. 21, 2022, 19 Pages.

Rudicell R.S., et al., "Enhanced Potency of a Broadly Neutralizing HIV-1 Antibody in Vitro Improves Protection Against Lentiviral Infection in Vivo," Journal of Virology, Nov. 2014, vol. 88(21), pp. 12669-12682.

Bouvin-Pley M., et al., "Drift of the HIV-1 Envelope Glycoprotein gp120 toward Increased Neutralization Resistance over the Course of the Epidemic: a Comprehensive Study Using the Most Potent and Broadly Neutralizing Monoclonal Antibodies," Journal of Virology, 2014, vol. 88(23), pp. 13910-13917.

Briney B., et al., Commonality Despite Exceptional Diversity in the Baseline Human Antibody Repertoire, Nature, 2019, vol. 566(7744), pp. 393-399.

Chuang G-T., et al., "Removal of Variable Domain N-Linked Glycosylation as a Means to Improve the Homogeneity of HIV-1 Broadly Neutralizing Antibodies," Jan. 2020, Monoclonal Antibodies(MABS), vol. 12(1), e1836719, pp. 1-13.

Dall'acqua W. F., et al., Properties of Human IgG1s Engineered for Enhanced Binding to the Neonatal Fc Receptor (FcRn), The Journal of Biological Chemistry, Aug. 18, 2006, vol. 281(33), pp. 23514-23524.

(Continued)

*Primary Examiner* — Misook Yu

(74) *Attorney, Agent, or Firm* — Kelly A. Gauger

(57) ABSTRACT

The present invention relates to a combination of cabotegravir or a pharmaceutically acceptable salt thereof and a gp120 binding protein. The present invention also provides a method of treatment human immunodeficiency virus (HIV) with the co-administration of a therapeutically effective amount of cabotegravir or a pharmaceutically acceptable salt thereof and a therapeutically effective amount of a gp120 binding protein.

15 Claims, No Drawings

Specification includes a Sequence Listing.

(56) References Cited

OTHER PUBLICATIONS

Ei Kiuchi, Journal of the Tokyo Pediatric Association, 2017, vol. 36, No. 2, pp. 33-38.

Hinton P. R., et al., "An Engineered Human Igg1 Antibody with Longer Serum Half-life," Journal of Immunology, Jan. 1, 2006, vol. 176(1), pp. 346-356.

Petkova S.B., et al., "Enhanced Half-Life of Genetically Engineered Human IgG 1 Antibodies in a Humanized FcRn Mouse Model: Potential Application in Humorally Mediated Autoimmune Disease," International Immunology, 2006, vol. 18, No. 12, pp. 1759-1769.

Zalevsky J., et al., "Enhanced Antibody Half-life Improves in Vivo Activity," Nature Biotechnology, Feb. 2010, vol. 28(2), pp. 157-159.

* cited by examiner

SEQUENCE LISTING

<160> NUMBER OF SEQ ID NOS: 22

<210> SEQ ID NO 1
<211> LENGTH: 122
<212> TYPE: PRT
<213> ORGANISM: Artificial Sequence
<220> FEATURE:
<223> OTHER INFORMATION: An amino acid sequence of the VH of the N6 mAb

<400> SEQUENCE: 1

```
Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110
```

```
Gly Gln Gly Thr Thr Val Val Val Ser Ala
        115                 120


<210> SEQ ID NO 2
<211> LENGTH: 103
<212> TYPE: PRT
<213> ORGANISM: Artificial Sequence
<220> FEATURE:
<223> OTHER INFORMATION: An amino acid sequence of the VL of the N6 mAb

<400> SEQUENCE: 2

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100


<210> SEQ ID NO 3
<211> LENGTH: 366
<212> TYPE: DNA
<213> ORGANISM: Artificial Sequence
<220> FEATURE:
<223> OTHER INFORMATION: A nucleic acid sequence encoding the VH of the
      N6 mAb

<400> SEQUENCE: 3

cgagcgcacc tggtacaatc agggactgcg atgaagaaac cgggggcctc agtaagagtc     60

tcctgccaga cctctggata cacctttacc gcccacatat tattttggtt ccgacaggcc    120

cccgggcgag gacttgagtg ggtggggtgg atcaagccac aatatggggc cgtgaatttt    180

ggtggtggtt ttcgggacag ggtcacattg actcgagacg tatatagaga gattgcgtac    240

atggacatca gaggccttaa acctgacgac acggccgtct attactgtgc gagagaccgt    300

tcctatggcg actcctcttg ggccttagat gcctggggac agggaacgac ggtcgtcgtc    360

tccgcg                                                               366


<210> SEQ ID NO 4
<211> LENGTH: 309
<212> TYPE: DNA
<213> ORGANISM: Artificial Sequence
<220> FEATURE:
<223> OTHER INFORMATION: A nucleic acid sequence encoding the VL of the
      N6 mAb

<400> SEQUENCE: 4

tacatccacg tgacccagtc tccgtcctcc ctgtctgtgt ctattggaga cagagtcacc     60

atcaattgcc agacgagtca gggtgttggc agtgacctac attggtatca acacaaaccg    120

gggagagccc ctaaactctt gatccaccat acctcttctg tggaagacgg tgtcccctca    180

agattcagcg gctctggatt tcacacatct tttaatctga ccatcagcga cctacaggct    240
```

```
gacgacattg ccacatatta ctgtcaagtt ttacaatttt tcggccgagg gagtcgactc    300

catattaaa                                                            309


<210> SEQ ID NO 5
<211> LENGTH: 452
<212> TYPE: PRT
<213> ORGANISM: Artificial Sequence
<220> FEATURE:
<223> OTHER INFORMATION: A heavy chain sequence including the N6 VH

<400> SEQUENCE: 5

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 6
<211> LENGTH: 1356
<212> TYPE: DNA
<213> ORGANISM: Artificial Sequence
<220> FEATURE:
<223> OTHER INFORMATION: A nucleic acid sequence encoding a heavy chain
      including the N6 VH

<400> SEQUENCE: 6

cgagcgcacc tggtacaatc agggactgcg atgaagaaac cgggggcctc agtaagagtc     60

tcctgccaga cctctggata caccttaacc gcccacatat tattttggtt ccgacaggcc    120

cccgggcgag gacttgagtg ggtggggtgg atcaagccac aatatggggc cgtgaatttt    180

ggtggtggtt ttcgggacag ggtcacattg actcgagacg tatatagaga gattgcgtac    240

atggacatca gaggccttaa acctgacgac acggccgtct attactgtgc gagagaccgt    300

tcctatggcg actcctcttg ggccttagat gcctggggac agggaacgac ggtcgtcgtc    360

tccgcggcgt cgaccaaggg cccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagaaagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgtgt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gatgagctga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                             1356
```

-continued

```
<210> SEQ ID NO 7
<211> LENGTH: 210
<212> TYPE: PRT
<213> ORGANISM: Artificial Sequence
<220> FEATURE:
<223> OTHER INFORMATION: A light chain sequence including the N6 VL

<400> SEQUENCE: 7

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210


<210> SEQ ID NO 8
<211> LENGTH: 630
<212> TYPE: DNA
<213> ORGANISM: Artificial Sequence
<220> FEATURE:
<223> OTHER INFORMATION: A nucleic acid sequence encoding a light chain
      including the N6 VH

<400> SEQUENCE: 8

tacatccacg tgacccagtc tccgtcctcc ctgtctgtgt ctattggaga cagagtcacc     60

atcaattgcc agacgagtca gggtgttggc agtgacctac attggtatca acacaaaccg    120

gggagagccc ctaaactctt gatccaccat acctcttctg tggaagacgg tgtcccctca    180

agattcagcg gctctggatt tcacacatct tttaatctga ccatcagcga cctacaggct    240

gacgacattg ccacatatta ctgtcaagtt ttacaatttt tcggccgagg gagtcgactc    300

catattaaac gtacggtggc tgcaccatct gtcttcatct tcccgccatc tgatgagcag    360

ttgaaatctg gaactgcctc tgttgtgtgc ctgctgaata acttctaccc cagagaagcc    420

aaagtgcagt ggaaggtgga caacgccctg cagagcggaa acagccagga aagcgtgaca    480
```

gagcaggatt ccaaggattc cacatacagc ctgagcagca cactgacact gtccaaggcc 540
gactacgaga agcacaaggt gtacgcctgc gaagtgacac accagggact gtcctcccct 600
gtgacaaaga gcttcaacag aggagaatgc 630

<210> SEQ ID NO 9
<211> LENGTH: 452
<212> TYPE: PRT
<213> ORGANISM: Artificial Sequence
<220> FEATURE:
<223> OTHER INFORMATION: A heavy chain sequence including the N6 VH as isolated from a human donor, which include polymorphism compared to SEQ ID NO: 5

<400> SEQUENCE: 9

Arg Ala His Leu Val Gln Ser Gly Thr Ala Met Lys Lys Pro Gly Ala
1 5 10 15

Ser Val Arg Val Ser Cys Gln Thr Ser Gly Tyr Thr Phe Thr Ala His
20 25 30

Ile Leu Phe Trp Phe Arg Gln Ala Pro Gly Arg Gly Leu Glu Trp Val
35 40 45

Gly Trp Ile Lys Pro Gln Tyr Gly Ala Val Asn Phe Gly Gly Gly Phe
50 55 60

Arg Asp Arg Val Thr Leu Thr Arg Asp Val Tyr Arg Glu Ile Ala Tyr
65 70 75 80

Met Asp Ile Arg Gly Leu Lys Pro Asp Asp Thr Ala Val Tyr Tyr Cys
85 90 95

Ala Arg Asp Arg Ser Tyr Gly Asp Ser Ser Trp Ala Leu Asp Ala Trp
100 105 110

Gly Gln Gly Thr Thr Val Val Val Ser Ala Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Glu Glu Tyr Lys Cys Lys Val Ser Asn Lys Ala Leu Pro Ala Pro

```
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 10
<211> LENGTH: 1356
<212> TYPE: DNA
<213> ORGANISM: Artificial Sequence
<220> FEATURE:
<223> OTHER INFORMATION: A sequence of the nucleic acid molecule
      encoding the N6 VH as isolated from a human donor

<400> SEQUENCE: 10

cgagcgcacc tggtacaatc agggactgcg atgaagaaac cgggggcctc agtaagagtc     60

tcctgccaga cctctggata cacctttacc gcccacatat tattttggtt ccgacaggcc    120

cccgggcgag gacttgagtg ggtggggtgg atcaagccac aatatggggc cgtgaatttt    180

ggtggtggtt ttcgggacag ggtcacattg actcgagacg tatatagaga gattgcgtac    240

atggacatca gaggccttaa acctgacgac acggccgtct attactgtgc gagagaccgt    300

tcctatggcg actcctcttg ggccttagat gcctggggac agggaacgac ggtcgtcgtc    360

tccgcggcct ccaccaaggg cccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagagagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgtgt ggtcagcgtc ctcaccgtcc tgcaccagga ctggctgaat    960

ggcgaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgccttg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260
```

aggtggcagc aggggaacgt cttctcatgc tccgtgatgc atgaggctct gcacaaccac 1320
tacacgcaga agagcctctc cctgtctccg ggtaaa 1356

<210> SEQ ID NO 11
<211> LENGTH: 366
<212> TYPE: DNA
<213> ORGANISM: Artificial Sequence
<220> FEATURE:
<223> OTHER INFORMATION: A nucleotide sequence encoding the N6 I1 VH intermediate

<400> SEQUENCE: 11
cgagggcact tggtgcagtc agggactgag gtgaagaaac cgggggcctc agtgagagtc 60
tcctgcgaga cttctggata caccttcacc gcctacattt tacattggtt ccgacaggcc 120
cccggacgag ggcttgagtg gatggggtgg atcaagccaa aatatggagc cgtcaattat 180
gctcatgcat ttcagggcag ggtcaccctg accagagaca tatatagaga cactgcatac 240
atggacttga gtggcctaag attcgacgac acggccgtct attactgtgc gagagatcgc 300
gtttatgacg attcgtcttg gcaattggat ccctggggcc agggaacttc ggtcatcgtc 360
tcctca 366

<210> SEQ ID NO 12
<211> LENGTH: 366
<212> TYPE: DNA
<213> ORGANISM: Artificial Sequence
<220> FEATURE:
<223> OTHER INFORMATION: A nucleotide sequence encoding the N6 I2 VH intermediate

<400> SEQUENCE: 12
cgagggcact tggtgcagtc agggactgag gtgaagaaac cgggggcctc agtgagagtc 60
tcctgcgaga cttctggata caccttcacc gcccacattt tacattggtt ccgacaggcc 120
cccggacgag ggcttgagtg gatggggtgg atcaagccaa aatatggagc cgtcaattat 180
gctcatgcat ttcagggcag ggtcaccctg accagagaca tatatagaga cactgcatac 240
atggacttga gtggcctaag attcgacgac acggccgtct attactgtgc gagagatcgc 300
gtttatgacg attcgtcttg gcaattggat ccctggggcc agggaacttc ggtcatcgtc 360
tcctca 366

<210> SEQ ID NO 13
<211> LENGTH: 366
<212> TYPE: DNA
<213> ORGANISM: Artificial Sequence
<220> FEATURE:
<223> OTHER INFORMATION: A nucleotide sequence encoding the N6 I3 VH intermediate.

<400> SEQUENCE: 13
cgagcgcact tggtgcagtc agggactgcg gtgaagaaac cgggggcctc agtgagagtc 60
tcctgcgaga cttctggata caccttcacc gcccacattt tatattggtt ccgacaggcc 120
cccggacgag ggcttgagtg ggtggggtgg atcaagccac aatatggggc cgtgaatttt 180
ggtggtggtt ttcggggcag ggtcaccctg accagagaca tatatagaga cactgcatac 240
atggacatca gtggcctaag attcgacgac acggccgtct attactgtgc gagagatcgc 300
tcctatgacg actcctcttg ggccttagat gcctggggac agggaacgac ggtcgtcgtc 360
tccgcg 366

<210> SEQ ID NO 14
<211> LENGTH: 366
<212> TYPE: DNA
<213> ORGANISM: Artificial Sequence
<220> FEATURE:
<223> OTHER INFORMATION: A nucleotide sequence encoding the N6 I4 VH intermediate.

<400> SEQUENCE: 14
cgagcgcacc tggtacaatc agggactgcg atgaagaaac cgggggcctc agtaagagtc 60
tcctgccaga cctctggata cacctttacc gcccacatat tattttggtt ccgacaggcc 120
cccgggcgag gacttgagtg ggtggggtgg atcaagccac aatatggggc cgtgaatttt 180
ggtggtggtt ttcgggacag ggtcacattg actcgagaca tatatagaga gattgcgtac 240
atggacatca gaggccttaa acttgacgac acggccgtct attactgtgc gagagaccgt 300
tcctatggcg actcctcttg ggccttagat gcctggggac agggaacgac ggtcgtcgtc 360
tccgcg 366

<210> SEQ ID NO 15
<211> LENGTH: 5
<212> TYPE: PRT
<213> ORGANISM: Artificial Sequence
<220> FEATURE:
<223> OTHER INFORMATION: An amino acid sequence of N6 CDRH1

<400> SEQUENCE: 15

Ala His Ile Leu Phe
1 5

<210> SEQ ID NO 16
<211> LENGTH: 17
<212> TYPE: PRT
<213> ORGANISM: Artificial Sequence
<220> FEATURE:
<223> OTHER INFORMATION: An amino acid sequence of N6 CDRH2

<400> SEQUENCE: 16

Trp Ile Lys Pro Gln Tyr Gly Ala Val Asn Phe Gly Gly Gly Phe Arg
1 5 10 15

Asp

<210> SEQ ID NO 17
<211> LENGTH: 13
<212> TYPE: PRT
<213> ORGANISM: Artificial Sequence
<220> FEATURE:
<223> OTHER INFORMATION: An amino acid sequence of N6 CDRH3

<400> SEQUENCE: 17

Asp Arg Ser Tyr Gly Asp Ser Ser Trp Ala Leu Asp Ala
1 5 10

<210> SEQ ID NO 18
<211> LENGTH: 11
<212> TYPE: PRT
<213> ORGANISM: Artificial Sequence
<220> FEATURE:
<223> OTHER INFORMATION: An amino acid sequence of N6 CDRL1

<400> SEQUENCE: 18

Gln Thr Ser Gln Gly Val Gly Ser Asp Leu His
1 5 10

<210> SEQ ID NO 19
<211> LENGTH: 7
<212> TYPE: PRT
<213> ORGANISM: Artificial Sequence
<220> FEATURE:
<223> OTHER INFORMATION: An amino acid sequence of N6 CDRL2

<400> SEQUENCE: 19

His Thr Ser Ser Val Glu Asp
1               5

<210> SEQ ID NO 20
<211> LENGTH: 5
<212> TYPE: PRT
<213> ORGANISM: Artificial Sequence
<220> FEATURE:
<223> OTHER INFORMATION: An amino acid sequence of N6 CDRL3

<400> SEQUENCE: 20

Gln Val Leu Gln Phe
1               5

<210> SEQ ID NO 21
<211> LENGTH: 471
<212> TYPE: PRT
<213> ORGANISM: Artificial Sequence
<220> FEATURE:
<223> OTHER INFORMATION: An amino acid sequence of the N6-LS heavy chain

<400> SEQUENCE: 21

Met Gly Trp Ser Cys Ile Ile Leu Phe Leu Val Ala Thr Ala Thr Gly
1               5                   10                  15

Val His Ser Arg Ala His Leu Val Gln Ser Gly Thr Ala Met Lys Lys
            20                  25                  30

Pro Gly Ala Ser Val Arg Val Ser Cys Gln Thr Ser Gly Tyr Thr Phe
        35                  40                  45

Thr Ala His Ile Leu Phe Trp Phe Arg Gln Ala Pro Gly Arg Gly Leu
    50                  55                  60

Glu Trp Val Gly Trp Ile Lys Pro Gln Tyr Gly Ala Val Asn Phe Gly
65                  70                  75                  80

Gly Gly Phe Arg Asp Arg Val Thr Leu Thr Arg Asp Val Tyr Arg Glu
                85                  90                  95

Ile Ala Tyr Met Asp Ile Arg Gly Leu Lys Pro Asp Asp Thr Ala Val
            100                 105                 110

Tyr Tyr Cys Ala Arg Asp Arg Ser Tyr Gly Asp Ser Ser Trp Ala Leu
        115                 120                 125

Asp Ala Trp Gly Gln Gly Thr Thr Val Val Val Ser Ala Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu

```
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Leu His Glu Ala Leu His Ser His Tyr Thr Gln Lys Ser
    450                 455                 460

Leu Ser Leu Ser Pro Gly Lys
465                 470


<210> SEQ ID NO 22
<211> LENGTH: 229
<212> TYPE: PRT
<213> ORGANISM: Artificial Sequence
<220> FEATURE:
<223> OTHER INFORMATION: An amino acid sequence of the N6-LS light chain

<400> SEQUENCE: 22

Met Gly Trp Ser Cys Ile Ile Leu Phe Leu Val Ala Thr Ala Thr Gly
1               5                   10                  15

Val His Ser Tyr Ile His Val Thr Gln Ser Pro Ser Ser Leu Ser Val
            20                  25                  30

Ser Ile Gly Asp Arg Val Thr Ile Asn Cys Gln Thr Ser Gln Gly Val
        35                  40                  45

Gly Ser Asp Leu His Trp Tyr Gln His Lys Pro Gly Arg Ala Pro Lys
    50                  55                  60

Leu Leu Ile His His Thr Ser Ser Val Glu Asp Gly Val Pro Ser Arg
65                  70                  75                  80

Phe Ser Gly Ser Gly Phe His Thr Ser Phe Asn Leu Thr Ile Ser Asp
                85                  90                  95

Leu Gln Ala Asp Asp Ile Ala Thr Tyr Tyr Cys Gln Val Leu Gln Phe
            100                 105                 110

Phe Gly Arg Gly Ser Arg Leu His Ile Lys Arg Thr Val Ala Ala Pro
```

-continued

```
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225
```

COMBINATION THERAPY

CROSS REFERENCE TO RELATED APPLICATIONS

The instant application claims priority to U.S. Provisional Patent Application Ser. No. 63/122,031 filed Dec. 7, 2020. The content of this application is incorporated by reference herein in its entirety.

SEQUENCE LISTING

The instant application contains a Sequence Listing, which has been submitted electronically in computer readable form in .txt format and is hereby incorporated by reference in its entirety. Said .txt file, created on Jun. 5, 2023, is named PU66989_US_Seqlist_created_20May2021.txt and is 27,738 bytes.

FIELD OF THE INVENTION

The invention relates to a method of treatment of Human Immunodeficiency Virus (HIV) infection. In particular, the invention relates to injectable combinations for the treatment of HIV infection.

BACKGROUND TO THE INVENTION

Human Immunodeficiency Virus type 1 (HIV-1) infection, and the resulting Acquired Immunodeficiency Syndrome (AIDS), remain threats to global public health, despite extensive efforts to develop anti-HIV-1 therapeutic agents. HIV-1 possesses a high mutation rate and a high frequency of recombination, which can result in rapid emergence of drug-resistant variants when the viral replication is not sufficiently inhibited. Iyidogan, P., & Anderson, K. S. (2014). *Current perspectives on HIV-*1 *antiretroviral drug resistance. Viruses,* 6 (10), 4095-4139. Problems with compliance to administration regimens, poor tolerability and previous exposure to antiretroviral therapy also place a patient in danger of developing HIV-1 drug resistant strains. Obasa A E, Mikasi S G, Brado D, et al. *Front Microbiol.* 2020; 11:438, Rossouw T M, Feucht U D, Melikian G, et al. *PLOS One.* 2015; 10 (7).

Highly active antiretroviral therapy (HAART), focuses on the co-administration of different drugs that inhibit viral replication by several mechanisms, specifically the HIV replication enzymes protease, integrase and transaminase. Inhibition of multiple mechanisms is necessary because propagation of the virus with resistance to a single agent becomes inhibited by the action of the other two agents. Shafer R W, Vuitton D A. *Biomed Pharmacother.* 1999 March; 53 (2): 73-86. Unfortunately, HIV drug resistance reduces or even eliminates the efficacy of multiple mechanism inhibition.

New strategies in the continued fight against HIV-1 drug resistance include antiretroviral therapies that focus on long acting formulations to reduce the number of dosage administrations. Another treatment strategy to avoid drug resistance includes neutralizing HIV-1 with broadly neutralizing antibodies (bNAbs). Neutralization is defined as the loss of infectivity that occurs when an antibody molecule binds a virion, the complete infective form of the virus outside a host cell. Specific bNAbs bind to HIV-1 envelope CD4-binding site of the virus membrane glycoprotein gp120, neutralizing the virion's ability to attach to and pass its RNA to T cells. Neutralizing antibodies have been developed that identify HIV-1 with varying recognition and sufficient areas of glycoprotein amino acid sequence conservation. Burton, D., Mascola, J. *Nat Immunol* 16, 571-576 (2015).

Currently, there remains a need in the art to develop HIV-1 therapeutic regimens that treat infection by increasing compliance to administration through fewer dosages.

SUMMARY OF THE INVENTION

According to a first aspect of the invention, there is provided a combination comprising cabotegravir or a pharmaceutically acceptable salt thereof and a gp120 binding protein wherein the gp120 binding protein neutralizes HIV-1.

According to a second aspect of the invention, there is provided a method of treating HIV in a human in need thereof comprising co-administering to a human a therapeutically effective amount of cabotegravir or a pharmaceutically acceptable salt thereof and a therapeutically effective amount of a gp120 binding protein wherein the gp120 binding protein neutralizes HIV-1.

According to a third aspect of the invention, there is provided a combination comprising cabotegravir or a pharmaceutically acceptable salt thereof and a gp120 binding protein wherein the gp120 binding protein neutralizes HIV-1 for the use in treatment of HIV.

According to a further aspect of the invention, there is provided use of cabotegravir or a pharmaceutically acceptable salt thereof and a gp120 binding protein as defined by claims 1 to 13, in the manufacture or a medicament for use in the treatment of HIV.

In a final aspect of the invention, there is provided a kit comprising cabotegravir or a pharmaceutically acceptable salt thereof and a gp120 binding protein that neutralizes HIV-1.

The present invention is advantageous in a number of respects. Specifically, the method of co-administration of cabotegravir or a pharmaceutically acceptable salt thereof and a gp120 binding protein may be safe, stable over an extended period of time and effective to treat HIV. A combination according to the invention comprising cabotegravir or a pharmaceutically acceptable salt thereof cabotegravir and a gp120 binding protein may provide protection against HIV infection and HIV neutralization.

DETAILED DESCRIPTION OF THE INVENTION

Definitions

As used herein, the term 'pharmaceutical composition' means a composition that is suitable for pharmaceutical use.

As used herein, the term "combination" refers to at least two therapeutic agents to be co-administered. As used herein the term "therapeutic agent" is understood to mean a substance that produces a desired effect in a tissue, system, animal, mammal, human, or other subject. For example, non-fixed dose combinations are contemplated.

As used herein, the term "co-administer" refers to simultaneous or sequential administration such that therapeutically effective amounts of the compounds are both present in the body of the patient. The term "co-administer" also refers to administration at the same time, as part of a non-fixed dose optionally in more than one formulation. The term "co-administer" also refers to administration at different schedules but could be administered within a given treatment cycle. Co-administration includes administration of pharmaceutical composition of integrase strand transfer inhibitors and gp120 binding protein, for example, administration of cabotegravir or a pharmaceutically acceptable salt thereof and a gp120 binding protein within seconds, minutes, hours, days or weeks of the administration of one another. For example, in some embodiments, a unit dose of one of the integrase strand transfer inhibitor or the gp120 binding protein is administered first, followed within seconds or minutes by administration of the other, by either the same or different routes.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Suitable pharmaceutically acceptable salts can include acid or base addition salts Suitable pharmaceutically acceptable salts of the invention include base addition salts.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

"Therapeutically effective amount" or "effective amount" refers to that amount of the compound being administered that will prevent a condition or will relieve to some extent one or more of the symptoms of the disorder being treated. Pharmaceutical compositions suitable for use herein include compositions wherein the active ingredients are contained in an amount sufficient enough to achieve the intended purpose. Determination of a therapeutically effective amount is well within the capability of those skilled in the art, especially in light of the detailed disclosure provided herein.

As used herein, the term "treatment" or "treating" in the context of therapeutic methods, refers to alleviating the specified condition, eliminating or reducing the symptoms of the condition, slowing or eliminating the progression, invasion, or spread of the condition and reducing or delaying the reoccurrence of the condition in a previously afflicted subject. The present invention further provides use of the compounds or compositions of the invention for the preparation of a medicament for the treatment of several conditions in a mammal (e.g., human) in need thereof.

As used herein, the term "parenteral" or "parenterally" in the context of therapeutic methods, refers to a route of administration of a pharmaceutical compound or composition other than by oral administration. Parenteral routes of administration suitable for use herein include injection, infusion, implantation or some other route other than the alimentary canal. Parenteral routes of injection administration include intravenous, intramuscular and subcutaneous.

As used herein, the term "gp120 binding protein" refers to antibodies and other protein constructs, such as domains, that are capable of binding to envelope glycoprotein GP120. The terms "gp120 binding protein" and "antigen binding protein" are used interchangeably herein. This does not include the natural cognate ligand or receptor. An example of a gp120 binding protein is the antibody N6 disclosed in U.S. Pat. No. 10,562,960 having the complementarity determining regions (CDR) SEQ ID Nos: 1, 2, 15, 16, 17, 18, 19 or 20. N6LS is a gp120 binding protein 960 having the complementarity determining regions (CDR) SEQ ID Nos: 1, 2, 15, 16, 17, 18, 19 or 20, and an IgG1 constant domain comprising M428L and N434S mutations.

As used herein, the term "antibody" is used herein in the broadest sense to refer to molecules with an immunoglobulin-like domain (for example IgG, IgM, IgA, IgD or IgE) and includes monoclonal or fragment thereof, recombinant, polyclonal, chimeric, human, humanised, broadly neutralizing, multispecific antibodies, including bispecific antibodies, and heteroconjugate antibodies; a single variable domain (e.g., a domain antibody (DAB)), antigen binding antibody fragments, Fab, $F(ab')_2$, Fv, disulphide linked Fv, single chain Fv, disulphide-linked scFv, diabodies, TANDABS, etc. and modified versions of any of the foregoing (for a summary of alternative "antibody" formats see Holliger and Hudson, Nature Biotechnology, 2005, Vol 23, No. 9, 1126-1136).

The term, full, whole or intact antibody, used interchangeably herein, refers to a heterotetrameric glycoprotein with an approximate molecular weight of 150,000 daltons. An intact antibody is composed of two identical heavy chains (HCs) and two identical light chains (LCs) linked by covalent disulphide bonds. This H2L2 structure folds to form three functional domains comprising two antigen-binding fragments, known as 'Fab' fragments, and a 'Fc' crystallisable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called $\mu$, $\alpha$, $\gamma$, $\varepsilon$ and $\delta$ respectively, each heavy chain can pair with either a K or $\lambda$ light chain. The majority of antibodies in the serum belong to the IgG class, there are four isotypes of human IgG (IgG1, IgG2, IgG3 and IgG4), the sequences of which differ mainly in their hinge region.

Fully human antibodies can be obtained using a variety of methods, for example using yeast-based libraries or transgenic animals (e.g. mice) that are capable of producing repertoires of human antibodies. Yeast presenting human antibodies on their surface that bind to an antigen of interest can be selected using FACS (Fluorescence-Activated Cell Sorting) based methods or by capture on beads using labelled antigens. Transgenic animals that have been modified to express human immunoglobulin genes can be immunised with an antigen of interest and antigen-specific human antibodies isolated using B-cell sorting techniques. Human antibodies produced using these techniques can then be characterised for desired properties such as affinity, developability and selectivity.

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

As used herein, the term "antigen binding site" refers to a site on an antigen binding protein that is capable of specifically binding to an antigen, this may be a single variable domain, or it may be paired VH/VL domains as can be found on a standard antibody. Single-chain Fv (ScFv) domains can also provide antigen-binding sites.

As used herein, the term "multi-specific antibody" refers to an antibody that comprises at least two different antigen binding sites. Each of these antigen-binding sites is capable of binding to a different epitope, which may be present on the same antigen or different antigens. The multi-specific antigen binding protein may have specificity for more than one antigen, for example two antigens, or three antigens, or four antigens.

Classification and formats of bispecific antibodies are comprehensively described in reviews by Labrijn et al 2019 and Brinkmann and Kontermann 2017. Bispecifics may be generally classified as having a symmetric or asymmetric architecture. Bispecifics may have an Fc or may be fragment-based (lacking an Fc). Fragment based bispecifics combine multiple antigen-binding antibody fragments in one molecule without an Fc region e.g. Fab-scFv, Fab-scFv2, orthogonal Fab-Fab, Fab-Fv, tandem scFc (e.g. BiTE and BiKE molecules), Diabody, DART, TandAb, scDiabody, tandem dAb etc.

Symmetric formats combine multiple binding specificities in a single polypeptide chain or single HL pair including Fc-fusion proteins of fragment-based formats and formats whereby antibody fragments are fused to regular antibody molecules. Examples of symmetric formats may include DVD-Ig, TVD-Ig, CODV-Ig, (scFv) 4-Fc, IgG-(scFv) 2, Tetravalent DART-Fc, F (ab) 4CrossMab, IgG-HC-scFv, IgG-LC-scFv, mAb-dAb etc.

Asymmetric formats retain as closely as possible the native architecture of natural antibodies by forcing correct HL chain pairing and/or promoting H chain heterodimerization during the co-expression of three (if common heavy or light chains are used) or four polypeptide chains e.g. Triomab, asymmetric reengineering technology immunoglobulin (ART-Ig), CrossMab, Biclonics common light chain, ZW1 common light chain, DuoBody and knobs into holes (KiH), DuetMab, κλ body, Xmab, YBODY, HET-mAb, HET-Fab, DART-Fc, SEEDbody, mouse/rat chimeric IgG.

Bispecific formats also include an antibody fused to a non-Ig scaffold such as Affimabs, Fynomabs, Zybodies, and Anticalin-IgG fusions, ImmTAC.

As used herein, the term "chimeric antigen receptor" ("CAR") as used herein, refers to an engineered receptor that consists of an extracellular antigen binding domain (usually derived from a monoclonal antibody or fragment thereof, e.g. a VH domain and a VL domain in the form of a scFv), optionally a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect T cell specificity for a desired cell-surface antigen, resulting in a CAR-T therapeutic.

The term "spacer region" as used herein, refers to an oligo- or polypeptide that functions to link the transmembrane domain to the target binding domain. This region may also be referred to as a "hinge region" or "stalk region". The size of the spacer can be varied depending on the position of the target epitope in order to maintain a set distance (e.g. 14 nm) upon CAR: target binding.

The term "transmembrane domain" as used herein, refers to the part of the CAR molecule that traverses the cell membrane.

The term "intracellular effector domain" (also referred to as the "signalling domain") as used herein refers to the domain in the CAR that is responsible for intracellular signalling following the binding of the antigen binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines.

It will be appreciated by a person skilled in the art that VH and/or VL domains disclosed herein may be incorporated, e.g. in the form of a scFv, into CAR-T therapeutics.

As used herein, the term "neutralises" as used throughout the present specification means that the biological activity of gp120 is reduced in the presence of an antigen binding protein as described herein in comparison to the activity gp120 in the absence of the antigen binding protein, in vitro or in vivo. Neutralisation may be due to one or more of blocking gp120 binding to its receptor, preventing gp120 from activating its receptor, down regulating gp120 or its receptor, or affecting effector functionality.

As used herein, the term "CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342:877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

| Kabat Numbering Scheme | | | | |
|---|---|---|---|---|
| | Kabat CDR | Chothia CDR | AbM CDR | Contact CDR |
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

Accordingly, an antigen binding protein is provided, which comprises any one or a combination of the following CDR amino acid sequences:

```
CDRH1 of SEQ ID NO 15:
AHILF

CDRH2 of SEQ ID NO 16:
WIKPQYGAVNFGGGFRD

CDRH3 of SEQ ID NO 17:
DRSYGDSSWALDA

CDRL1 of SEQ ID NO 18:
QTSQGVGSDLH

CDRL2 of SEQ ID NO 19:
HTSSVED

CDRL3 of SEQ ID NO 20:
QVLQF
```

In an embodiment of the invention, CDRs may be modified by at least one amino acid substitution, deletion or addition, wherein the variant antigen binding protein substantially retains the biological characteristics of the unmodified protein, such as N6 or N6LS.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in Table 2 below.

TABLE 2

| conservative substitutions | |
|---|---|
| Side chain | Members |
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the flanking residues that comprise the CDR as part of alternative definition(s) e.g. Kabat or Chothia, may be substituted with a conservative amino acid residue.

Such antigen binding proteins comprising variant CDRs as described above may be referred to herein as "functional CDR variants".

As used herein, the term "epitope" as used herein refers to that portion of the antigen that makes contact with a particular binding domain of the antigen binding protein, also known as the paratope. An epitope may be linear or conformational/discontinuous. A conformational or discontinuous epitope comprises amino acid residues that are separated by other sequences, i.e. not in a continuous sequence in the antigen's primary sequence assembled by tertiary folding of the polypeptide chain. Although the residues may be from different regions of the polypeptide chain, they are in close proximity in the three dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. Epitope mapping can be carried out using various techniques known to persons skilled in the art as described in publications such as Methods in Molecular Biology 'Epitope Mapping Protocols', Mike Schutkowski and Ulrich Reineke (volume 524, 2009) and Johan Rockberg and Johan Nilvebrant (volume 1785, 2018). Exemplary methods include peptide based approaches such as pepscan whereby a series of overlapping peptides are screened for binding using techniques such as ELISA or by in vitro display of large libraries of peptides or protein mutants, e.g. on phage. Detailed epitope information can be determined by structural techniques including X-ray crystallography, solution nuclear magnetic resonance (NMR) spectroscopy and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

Competition between the gp120 binding protein of the invention and a reference gp120 binding protein, e.g. a reference antibody, may be determined by one or more techniques known to the skilled person such as ELISA, FMAT, Surface Plasmon Resonance (SPR) or FORTEBIO OCTET Bio-Layer Interferometry (BLI). Such techniques may also be referred to as epitope binning. There are several possible reasons for this competition: the two proteins may bind to the same or overlapping epitopes, there may be steric inhibition of binding, or binding of the first protein may induce a conformational change in the antigen that prevents or reduces binding of the second protein.

The reduction or inhibition in biological activity may be partial or total. In an embodiment of the invention, administration of a therapeutically effective amount of a disclosed antibody or antigen binding fragment that binds to gpl20 can reduce or inhibit an HIV-1 infection (for example, as measured by infection of cells, or by number or percentage of subjects infected by HIV-1, or by an increase in the survival time of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable HIV-1 infection), as compared to a suitable control. Neutralisation may be determined or measured using one or more assays known to the skilled person or as described herein.

"Percent identity" between a query nucleic acid sequence and a subject nucleic acid sequence is the "Identities" value, expressed as a percentage, that is calculated using a suitable algorithm or software, such as BLASTN, FASTA, DNASTAR Lasergene, GeneDoc, Bioedit, EMBOSS needle or EMBOSS infoalign, over the entire length of the query sequence after a pair-wise global sequence alignment has been performed using a suitable algorithm or software, such as BLASTN, FASTA, ClustalW, MUSCLE, MAFFT, EMBOSS Needle, T-Coffee, and DNASTAR Lasergene. Importantly, a query nucleic acid sequence may be described by a nucleic acid sequence identified in one or more claims herein.

"Percent identity" between a query amino acid sequence and a subject amino acid sequence is the "Identities" or "Identical" value, expressed as a percentage, that is calculated using a suitable algorithm or software, such as BLASTP, FASTA, DNASTAR Lasergene, GeneDoc, Bioedit, EMBOSS needle or EMBOSS infoalign, over the entire length of the query sequence after a pair-wise global sequence alignment has been performed using a suitable algorithm/software such as BLASTP, FASTA, ClustalW, MUSCLE, MAFFT, EMBOSS Needle, T-Coffee, and DNASTAR Lasergene. Importantly, a query amino acid sequence may be described by an amino acid sequence identified in one or more claims herein.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

The % identity may be determined across the entire length of the query sequence, including the CDRs. Alternatively, the % identity may exclude one or more or all of the CDRs, for example all of the CDRs are 100% identical to the subject sequence and the % identity variation is in the remaining portion of the query sequence, e.g. the framework sequence, so that the CDR sequences are fixed and intact.

The variant sequence substantially retains the biological characteristics of the unmodified protein, such as gp120.

For sequence variation, the VH or VL (or HC or LC) sequence may be a variant sequence with up to 10 amino acid substitutions, additions or deletions. For example, the variant sequence may have up to 9, 8, 7, 6, 5, 4, 3, 2 or 1 amino acid substitution(s), addition(s) or deletion(s).

The HC sequence may be a variant sequence with up to 20% sequence variation.

The LC sequence may be a variant sequence with up to 20% sequence variation.

The sequence variation may exclude one or more or all of the CDRs, for example the CDRs are the same as the VH or VL (or HC or LC) sequence and the variation is in the remaining portion of the VH or VL (or HC or LC) sequence, so that the CDR sequences are fixed and intact.

Typically, the variation is a substitution, particularly a conservative substitution, for example as shown in Table 2.

The variant sequence substantially retains the biological characteristics of the unmodified protein, such as gp120.

As used herein, the term "genetic barrier to resistance" refers to the number of mutations required to confer resistance to a pharmaceutical composition. A pharmaceutical composition with a low genetic barrier to resistance will become less effective after the virus mutates or have a low number of mutations. A pharmaceutical composition with a high genetic barrier to resistance will not lose biological activity against the virus even after several mutations.

As used herein, the term "integrase strand transfer inhibitor" refers to a class of antiretroviral drugs designed to block the action of integrase, a viral enzyme that inserts the viral genome into the DNA of the host cell. While not being bound by theory, inhibition of HIV genome integration stops retroviral replication halting the further spread of the virus.

STATEMENT OF THE INVENTION

The present invention, a combination and a method, may be used to treat or neutralize HIV which unless further clarified is intended to mean HIV-1. As an alternative embodiment, the method and combination may also be effective against HIV-2, or against patients having dual HIV-1/HIV-2 infection.

According to a first aspect, the present invention provides a combination comprising cabotegravir or a pharmaceutically acceptable salt thereof and a gp120 binding protein wherein the gp120 binding protein neutralizes HIV-1.

Cabotegravir (N-((2,4-Difluorophenyl)methyl)-6-hydroxy-3-methyl-5,7-dioxo-2,3,5,7,11,11a hexahydro (1,3) oxazolo (3,2-a)pyrido (1,2-d) pyrazine-8-carboxamide) is described in U.S. Pat. No. 8,129,385 in example Z-1. Cabotegravir is an integrase strand transfer inhibitor (INSTI) that exhibits subnanomolar potency and antiviral activity against a broad range of HIV-1 strains. Oral administration of Cabotegravir has exhibited acceptable safety and tolerability profiles, a long half-life, and few drug-drug interactions. Cabotegravir has been demonstrated to be efficacious in treatment and prevention of HIV both in oral and parenteral dosage forms, see for instance, Margolis D A, Brinson C C, Eron J J, et al. 744 and Rilpivirine as Two Drug Oral Maintenance Therapy: LAI116482 (LATTE) Week 48 Results. 21st Conference on Retroviruses and Opportunistic Infections (CROI); Mar. 3-6, 2014; Boston, MA, Margolis D A, Podzamczer D, Stellbrink H-J, et al. Cabotegravir+Rilpivirine as Long-Acting Maintenance Therapy: LATTE-2 Week 48 Results. 21st International AIDS Conference; Jul. 18-22, 2016; Durban, South Africa, Abstract THAB0206 LB. Levin: Conference reports for National AIDS Treatment Advocacy Project (NATAP); 2016, and Markowitz M, Frank I, Grant R, et al. ECLAIR: Phase 2A Safety and PK Study of Cabotegravir LA in HIV-Uninfected Men. Abstract presented at 23rd Conference on Retroviruses and Opportunistic Infections (CROI); Feb. 22-25, 2016; Boston, MA. Bictegravir is also an integrase strand transfer inhibitor. Herein disclosed is a combination of bictegravir with a gp120 binding molecule.

In an embodiment of the invention, cabotegravir is present as a free acid. In an alternative embodiment of the invention, Cabotegravir is present as a sodium salt.

In an embodiment of the invention, cabotegravir or pharmaceutically acceptable salt thereof is presented as a pharmaceutical composition. The present cabotegravir or pharmaceutically acceptable salt thereof can be administered orally or parenterally. In the case of oral administration, the cabotegravir or pharmaceutically acceptable salt thereof can be also used as a conventional preparation, for example, as any dosage form of a solid agent such as tablets, powders, granules, capsules and the like; an aqueous agent; an oily suspension; or a liquid agent such as syrup and elixir.

In the case of parenteral administration, the compound can be used as an aqueous or oily suspension injectable, or a nasal drop. Upon preparation of it, conventional excipients, binders, lubricants, aqueous solvents, oily solvents, emulsifiers, suspending agents, preservatives, stabilizers and the like may be used.

In an embodiment of the invention, the pharmaceutical composition comprises cabotegravir or pharmaceutically acceptable salt thereof and a surfactant system. In an embodiment of the invention, the surfactant system further comprises a combination of polymers providing for the release of cabotegravir or pharmaceutically acceptable salt thereof over a period of one to three months. A suitable combination of polymers is, for example, polysorbate 20 and polyethylene glycol 3350. In an embodiment of the invention, the surfactant system comprises mannitol. In an embodiment of the invention, the cabotegravir is nanomilled to <200 nm.

In an embodiment of the invention, the dose of cabotegravir or pharmaceutically acceptable salt thereof to be administered orally is be calculated on a basis of about 1 mg/day to about 50 mg/day, preferably 5 mg/day to about 30 mg/day, more preferably 30 mg/day.

In another embodiment of the invention, the dose of cabotegravir or pharmaceutically acceptable salt thereof is to be administered parenterally at a dose of about 10 mg to about 1000 mg per week, per one month, per two months, per three months, or per six months. According to one embodiment, the compound or salt thereof is administered at either 400 mg, 600 mg, or 900 mg.

In an embodiment of the invention, the pharmaceutical composition as defined above may be administered daily, weekly, monthly, bi-monthly (once every two months) or tri-monthly (once every three months)

In an embodiment of the invention, the combination provides a gp120 binding protein. GP120 binding proteins bind to the exposed envelope glycoprotein 120 found on the HIV virion and inhibit the virion from attaching to CD4 receptor found on the cell surface of T cells. By blocking binding to the CD4 receptor, the virion is unable to bind with T cell coreceptors, fuse the virion membrane with the T cell membrane and push the virion's genetic information into the cell.

In an embodiment of the invention, the gp120 binding protein comprises a monoclonal antibody or a fragment thereof. The term "monoclonal antibody" indicates the character of the antibody as being obtained from a substantially homogeneous population of antibodies and is not to be construed as requiring production of the antibody by any particular method. In an embodiment of the invention, the monoclonal antibody has a VH and VL as defined above.

In an embodiment of the invention, the gp120 binding protein comprises a heavy chain variable region (VH) comprising a heavy chain complementarity determining region (CDRH) having a CDRH1 amino acid sequence that comprises a sequence that is at least 80%, 85%, 90%, 95%, 98% or 99% identical to SEQ ID NO: 15, a CDRH2 amino acid sequence that comprises a sequence that is at least 80%, 85%, 90%, 95%, 98% or 99% identical to SEQ ID NO: 16, and a CDRH3 amino acid sequence that comprises a sequence that is at least 80%, 85%, 90%, 95%, 98% or 99% identical to SEQ ID NO: 17, and a light chain variable region (VL) comprising a light chain complementarity determining region (CDRL) having a CDRL1 amino acid that comprises a sequence that is at least 80%, 85%, 90%, 95%, 98% or 99% identical to SEQ ID NO: 18, a CDRL2 amino acid sequence that comprises a sequence that is at least 80%, 85%, 90%, 95%, 98% or 99% identical to SEQ ID NO: 19, and a CDRHL 3 amino acid sequence that comprises a sequence that is at least 80%, 85%, 90%, 95%, 98% or 99% identical to SEQ ID NO: 20.

In an embodiment of the invention, the gp120 binding protein comprises a VH comprising a heavy chain complementarity determining region (CDRH) having the CDRH1 amino acid sequence as shown in SEQ ID NO: 15, the CDRH2 amino acid sequence as shown in SEQ ID NO: 16, and the CDRH3 amino acid sequence as shown in SEQ ID NO: 17, and a VL comprising a light chain complementarity determining region (CDRL) having the CDRL1 amino acid sequence as shown in SEQ ID NO: 18, the CDRHL amino acid sequence as shown in SEQ ID NO: 19, and the CDRHL 3 amino acid sequence shown in in SEQ ID NO: 20.

In an embodiment of the invention, the gp120 binding protein comprises comprise a variable heavy chain region amino acid sequence that comprises a sequence that is at least 80%, 85%, 90%, 95%, 98%, or 99% identical to SEQ ID NO: 1. In an embodiment of the invention, the gp120 binding protein comprises a variable heavy chain region amino acid sequence as shown in SEQ ID NO: 1.

In an embodiment of the invention, the gp120 binding protein comprises comprise a variable light chain region amino acid sequence that comprises a sequence that is at least 80%, 85%, 90%, 95%, 98%, or 99% identical to SEQ ID NO: 2. In an embodiment of the invention, the gp120 binding protein comprises a variable heavy chain region amino acid sequence as shown in SEQ ID NO: 2.

In an embodiment of the invention, the gp120 binding protein comprises comprise a variable heavy chain region amino acid sequence that comprises a sequence that is at least 80%, 85%, 90%, 95%, 98%, or 99% identical to SEQ ID NO: 1 and a variable light chain region amino acid sequence that comprises a sequence that is at least 80%, 85%, 90%, 95%, 98%, or 99% identical to SEQ ID NO: 2. In an embodiment of the invention, the gp120 binding protein comprises a variable heavy chain region amino acid sequence as shown in SEQ ID NO: 1 and a variable heavy chain region amino acid sequence as shown in SEQ ID NO: 2.

In an embodiment of the invention, the gp120 binding protein may have a CDRH1 with the amino acid sequence at least 80%, 85%, 90%, 95%, 98%, or 99% identical to SEQ ID NO: 15 and a CDRH2 with the amino acid sequence at least 80%, 85%, 90%, 95%, 98%, or 99% identical to SEQ ID NO: 16. In an embodiment of the invention, the gp120 binding protein may have a CDRH1 with the amino acid sequence at least 80%, 85%, 90%, 95%, 98%, or 99% identical to SEQ ID NO: 15 and a CDRH3 with the amino acid sequence at least 80%, 85%, 90%, 95%, 98%, or 99% identical to SEQ ID NO: 17. In an embodiment of the invention, the gp120 binding protein may have a CDRH2 with the amino acid sequence at least 80%, 85%, 90%, 95%, 98%, or 99% identical to SEQ ID NO: 16 and a CDRH3 with the amino acid sequence at least 80%, 85%, 90%, 95%, 98%, or 99% identical to SEQ ID NO: 17.

In an embodiment of the invention, the gp120 binding protein may have a CDRH1 with the amino acid sequence of SEQ ID NO: 15 and a CDRH2 with the amino acid sequence of SEQ ID NO: 16. In an embodiment of the invention, the gp120 binding protein may have a CDRH1 with the amino acid sequence of SEQ ID NO: 15 and a CDRH3 with the amino acid sequence of SEQ ID NO: 17. In an embodiment of the invention, the gp120 binding protein may have a CDRH2 with the amino acid sequence of SEQ ID NO: 16 and a CDRH3 with the amino acid sequence of SEQ ID NO: 17.

In an embodiment of the invention, the gp120 binding protein may have a CDRL1 with the amino acid sequence at least 80%, 85%, 90%, 95%, 98%, or 99% identical to SEQ ID NO: 18 and a CDRL2 with the amino acid sequence at least 80%, 85%, 90%, 95%, 98%, or 99% identical to SEQ ID NO: 19. In an embodiment of the invention, the gp120 binding protein may have a CDRL1 with the amino acid sequence at least 80%, 85%, 90%, 95%, 98%, or 99% identical to SEQ ID NO: 18 and a CDRL3 with the amino acid sequence at least 80%, 85%, 90%, 95%, 98%, or 99% identical to SEQ ID NO: 20. In an embodiment of the invention, the gp120 binding protein may have a CDRL2 with the amino acid sequence at least 80%, 85%, 90%, 95%, 98%, or 99% identical to SEQ ID NO: 19 and a CDRL3 with the amino acid sequence at least 80%, 85%, 90%, 95%, 98%, or 99% identical to SEQ ID NO: 20.

In an embodiment of the invention, the gp120 binding protein may have a CDRL1 with the amino acid sequence of SEQ ID NO: 18 and a CDRL2 with the amino acid sequence of SEQ ID NO: 19. In an embodiment of the invention, the gp120 binding protein may have a CDRL1 with the amino acid sequence of SEQ ID NO: 18 and a CDRL3 with the amino acid sequence of SEQ ID NO: 20. In an embodiment of the invention, the gp120 binding protein may have a CDRL2 with the amino acid sequence of SEQ ID NO: 19 and a CDRL3 with the amino acid sequence of SEQ ID NO: 20.

In an embodiment of the invention, the gp120 binding protein in an antigen binding fragment. In an embodiment of the invention, the antigen binding fragment has a VH and a VL as defined above. In an embodiment of the invention, the antigen binding fragment comprises a Fv, Fab, F(ab')$_2$, scFV or a scFV$_2$ fragment. Further examples of antigen binding fragments include but are not limited to Fv, Fab, Fab', Fab'-SH, F(ab')2, diabodies, linear antibodies, single-chain antibody molecules (e.g. scFV) and multispecific antibodies formed from antibody fragments.

In an embodiment of the invention, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al, J Immunol, 176:346-356, 2006); M428L and N434S (the "LS" mutation, see, e.g., Zalevsky, et al, Nature Biotechnology, 28:157-159, 2010); N434A (see, e.g., Petkova et al, Int. Immunol, 18:1759-1769, 2006); T307A, E380A, and N434A (see, e.g., Petkova et al, Int. Immunol, 18:1759-1769, 2006); and M252Y, S254T, and T256E (see, e.g., Dall'Acqua et al, J. Biol. Chem., 281:23514-23524, 2006). The disclosed antibodies and antigen binding fragments can be linked to a Fc polypeptide including any of the substitutions listed above, for example, the Fc polypeptide can include the M428L and N434S substitutions. Thus, in an embodiment of the invention, the monoclonal antibody comprises a recombinant constant domain comprising a modification that increases binding to a neonatal Fc receptor relative to an unmodified constant domain, wherein the recombinant domain is an IgG1 constant domain comprising M428L and N434S mutations.

In an embodiment of the invention, the constant region of the antibody includes one of more amino acid substitutions to optimize antibody-dependent cell-mediated cytotoxicity (ADCC). ADCC is mediated primarily through a set of closely related Fey receptors. In some embodiments, the antibody includes one or more amino acid substitutions that increase binding to FcγRIIIa. Several such substitutions are known to the person of ordinary skill in the art, such as substitutions at IgG constant regions S239D and I332E (see, e.g., Lazar et al, Proc. Natl, Acad. Sci. U.S.A., 103:4005-4010, 2006); and S239D, A330L, and I332E (see, e.g., Lazar et al, Proc. Natl, Acad. Sci. U.S.A., 103:4005-4010, 2006).

In an embodiment of the invention, combinations of the above substitutions are also included, to generate an IgG constant region with increased binding to FcRn and FcγRIIIa. The combinations increase antibody half-life and ADCC. For example, such combination include antibodies with the following amino acid substitution in the Fc region: (1) S239D/1332E and T250Q/M428L; (2) S239D/1332E and M428L/N434S; (3) S239D/I332E and N434A; (4) S239D/I332E and T307A/E380A/N434A; (5) S239D/1332E and M252Y/S254T/T256E; (6) S239D/A330L/1332E and 250Q/M428L; (7) S239D/A330L/1332E and M428L/N434S; (8) S239D/A330L/1332E and N434A; (9) S239D/A330L/1332E and T307A/E380A/N434A; or (10) S239D/A330L/1332E and M252Y/S254T/T256E. In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In an embodiment of the invention, the gp120 binding protein is provided as a gp120 binding protein composition. In an embodiment, the gp120 binding protein composition includes one or more of the gp120-specific antibody, antigen binding fragment, conjugate, CAR, T cell expressing a CAR, or nucleic acid molecule encoding such molecules, that are disclosed herein in a carrier. The gp120 binding protein compositions are useful, for example, for the treatment or detection of HIV-1 infection. The gp120 binding protein compositions can be prepared in unit dosage forms for administration to a subject. The amount and timing of administration are at the discretion of the treating physician to achieve the desired purposes. The gp120-specific antibody, antigen binding fragment, conjugate, CAR, T cell expressing a CAR, or nucleic acid molecule encoding such molecules can be formulated for systemic or local administration. In one example, the gp120-specific antibody, antigen binding fragment, conjugate, CAR, T cell expressing a CAR, or nucleic acid molecule encoding such molecules, is formulated for parenteral administration, such as intravenous administration.

In an embodiment of the invention, the gp120 binding protein compositions comprise an antibody, antigen binding fragment, or conjugate thereof, in at least 70% (such as at least 75%, at least 80%, at least 85%, at least 90%, at least 95%, at least 96%, at least 97%, at least 98% or at least 99% purity. In certain embodiments, the compositions contain less than 10% (such as less than 5%, less than 4%, less than 3%, less than 2%, less than 1%, less than 0.5%, or even less) of macromolecular contaminants, such as other mammalian (e.g., human) proteins The gp120 binding protein compositions for administration can include a solution of the gpl20-specific antibody, antigen binding fragment, conjugate, CAR, T cell expressing a CAR, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely and will be selected primarily based on fluid volumes, viscosities, body weight and the like in accordance with the particular mode of administration selected and the subject's needs.

A typical gp120 binding protein composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as Remington's Pharmaceutical Science, 22nd ed., Pharmaceutical Press, London, UK (2012). In some embodiments, the composition can be a liquid formulation including one or more antibodies, antigen binding fragments (such as an antibody or antigen binding fragment that specifically binds to gpl20), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of 0.5 to 15 mg/kg of body weight. Considerable experience is available in the art in the administration of antibody drugs, which have been marketed in the U.S. since the approval of RITUXAN® in 1997. Antibodies, antigen binding fragments, conjugates, or a nucleic acid encoding such molecules, can be administered by slow infusion, rather than in an intravenous push or bolus.

In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In an embodiment of the invention, the gp120 binding protein or gp120 binding protein composition, as defined above, is administered at a dose in the range of from about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. In an embodiment of the invention, the gp120 binding protein or gp120 binding protein composition can be administered to a subject at a dose of from about 0.5 to about 40 mg/kg, such as about 1 to about 30, about 1 to about 20, about 1 to about 15, about 1 to about 10, about 1 to about 5, about 1 to about 3, about 0.5 to about 40 mg/kg, such as about 0.5 to about 30, about 0.5 to about 20, about 0.5 to about 15, about 0.5 to about 10, about 0.5 to about 5, about 0.5 to about 3, about 3 to about 7, about 8 to about 12, about 15 to about 25, about 18 to about 22, about 28 to about 32, about 10 to about 20, about 5 to about 15, or about 20 to about 40 mg/kg. The doses described herein can be administered according to the dosing frequency/frequency of administration described herein, including without limitation daily, weekly, every 2 weeks, monthly, every other month, every 3 months, every 4 months, every 5 months, every 6 months, every 9 months, or every 12 months.

In an embodiment of the invention, the combination is be administered by any suitable means. In one embodiment, the combination is administered parenterally. The combination may be administered in the form of an injectable. In an embodiment of the invention, the combination is administered intramuscularly. In an embodiment of the invention, the combination is administered subcutaneously. In an embodiment of the invention, the combination is administered intravenously.

In an embodiment of the invention, the combination is administered to a human once every month, once every 2 months or once every 3 months. In an embodiment of the invention, the combination is administered once every month. In an embodiment of the invention, the combination is administered once every 2 months. In an embodiment of the invention, the combination is administered once every 3 months. In an embodiment of the invention, the combination is administered once every 6 months.

In an embodiment of the invention, the cabotegravir and the gp120 binding protein are self-administered by a human. The term "self-administered", as used herein, means administration by someone other than a healthcare professional, for example, a patient may administer the pharmaceutical composition to themselves, or someone else, other than a healthcare professional may administer the pharmaceutical composition to the patient. In another embodiment, the cabotegravir and the gp120 binding protein are administered by a health-care professional.

In an embodiment of the invention, the gp120 binding protein is a broadly neutralizing antibody (bNAb). Broadly neutralizing antibodies to HIV-1 are distinct from other antibodies to HIV-1 in that they neutralize a high percentage of the many types of HIV-1 in circulation. In some embodiments, broadly neutralizing antibodies to HIV-1 are distinct from other antibodies to HIV-1 in that they neutralize a high percentage (such as at least 90%, at least 95%, at least 96%, at least 97%, at least 98%, at least 99%) of the many types of HIV-1 in circulation.

According to a second aspect of the invention, the present invention provides a method of treating HIV in a human in need thereof comprising co-administering to a human a therapeutically effective amount of cabotegravir or a pharmaceutically acceptable salt thereof and a therapeutically effective amount of a gp120 binding protein the neutralizes HIV-1. The cabotegravir is as described above in the first aspect. The gp120 binding protein is as described above in the first aspect.

In an embodiment of the invention, the method provides the gp120 binding protein comprises a monoclonal antibody or fragment thereof.

In an embodiment of the invention, the method provides the gp120 comprises a heavy chain variable region (VH) comprising a heavy chain complementarity determining region (CDRH) having a CDRH1 amino acid sequence that comprises a sequence that is at least 80%, 85%, 90%, 95%, 98% or 99% identical to SEQ ID NO: 15, a CDRH2 amino acid sequence that comprises a sequence that is at least 80%, 85%, 90%, 95%, 98% or 99% identical to SEQ ID NO: 16, and a CDRH3 amino acid sequence that comprises a sequence that is at least 80%, 85%, 90%, 95%, 98% or 99% identical to SEQ ID NO: 17, and a light chain variable region (VL) comprising a light chain complementarity determining region (CDRL) having a CDRL1 amino acid that comprises a sequence that is at least 80%, 85%, 90%, 95%, 98% or 99% identical to SEQ ID NO: 18, a CDRL2 amino acid sequence that comprises a sequence that is at least 80%, 85%, 90%, 95%, 98% or 99% identical to SEQ ID NO: 19, and a CDRHL 3 amino acid sequence that comprises a sequence that is at least 80%, 85%, 90%, 95%, 98% or 99% identical to SEQ ID NO: 20.

In an embodiment of the invention, the method provides the gp120 binding protein comprises a VH comprising a heavy chain complementarity determining region (CDRH) having the CDRH1 amino acid sequence shown in in SEQ ID NO: 15, the CDRH2 amino acid sequence shown in in SEQ ID NO: 16, and the CDRH3 amino acid sequence shown in in SEQ ID NO: 17, and a VL comprising a light chain complementarity determining region (CDRL) having the CDRL1 amino acid sequence shown in in SEQ ID NO: 18, the CDRHL amino acid sequence shown in in SEQ ID NO: 19, and the CDRHL 3 amino acid sequence shown in in SEQ ID NO: 20.

In an embodiment of the invention, the method provides the gp120 binding protein comprises a variable heavy chain region amino acid sequence that comprises a sequence that is at least 80%, 85%, 90%, 95%, 98%, or 99% identical to SEQ ID NO: 1. In an embodiment of the invention, the method provides the gp120 binding protein comprises a variable heavy chain region amino acid sequence as shown in SEQ ID NO: 1.

In an embodiment of the invention, the method provides the gp120 binding protein comprises a variable light chain region amino acid sequence that comprises a sequence that is at least 80%, 85%, 90%, 95%, 98%, or 99% identical to SEQ ID NO: 2. In an embodiment of the invention, the method provides the gp120 binding protein comprises a variable light chain region amino acid sequence shown in SEQ ID NO: 2.

In an embodiment of the invention, the method provides the gp120 binding protein comprises a variable heavy chain region amino acid sequence that comprises a sequence that is at least 80%, 85%, 90%, 95%, 98%, or 99% identical to SEQ ID NO: 1 and a sequence that is at least 80%, 85%, 90%, 95%, 98%, or 99% identical to SEQ ID NO: 2.

In an embodiment of the invention, the method provides the gp120 binding protein comprises a variable heavy chain region amino acid sequence as shown in SEQ ID NO: 1 and a gp120 binding protein comprises a variable light chain region amino acid sequence shown in SEQ ID NO: 2.

In an embodiment of the invention, the method provides the gp120 binding protein comprises an antigen binding fragment. In an embodiment of the invention, the method provides the antigen binding is a Fv, Fab, F(ab')$_2$, scFV or a scFV$_2$ fragment.

In an embodiment of the invention, the method provides the monoclonal antibody comprises a recombinant constant domain comprising a modification that increases binding to a neonatal Fc receptor relative to an unmodified constant domain, wherein the recombinant domain is an IgG1 constant domain comprising M428L and N434S mutations.

In an embodiment of the invention, the method provides for the co-administration of cabotegravir or a pharmaceutically acceptable salt thereof and a gp120 binding protein. In an embodiment of the invention, the method provides co-administration of the cabotegravir and the gp120 binding protein is sequential. In an embodiment of the invention, the method provides co-administration of the cabotegravir and the gp120 binding protein is simultaneous. In an embodiment of the invention, the co-administration is not simultaneous. The compounds may be administered at different schedules but could be administered within a given treatment cycle. In an embodiment of the invention, the co-administration of the compounds occurs within seconds, minutes, hours, days, weeks or months of each other. In an embodiment, co-administration occurs by any suitable means. In an embodiment of the invention, the method comprises administering the cabotegravir and the gp120 binding protein parenterally. The cabotegravir and the gp120 binding protein parenterally may be administered in the form of injectables. In an embodiment of the invention, each injectable may independently be administered intramuscularly. In an embodiment of the invention, each injectable may independently be administered subcutaneously. In an embodiment of the invention, the method comprises co-administering the cabotegravir and the gp120 binding protein wherein each injectable may independently be administered intravenously.

In an embodiment of the invention, the method comprises administering the cabotegravir and the gp120 binding protein to the human once every month, once every 2 months, once every 3 months, or once every 6 months.

According to a third aspect of the invention, there is provided a combination comprising cabotegravir or a pharmaceutically acceptable salt thereof and a gp120 binding protein, as described above, wherein the gp120 binding protein neutralizes HIV-1 for the use in treatment of HIV.

In an embodiment of the invention, the combination for use provides the gp120 binding protein comprises a monoclonal antibody or fragment thereof.

In an embodiment of the invention, the combination for use provides the gp120 binding protein comprises a heavy chain variable region (VH) comprising a heavy chain complementarity determining region (CDRH) having a CDRH1 amino acid sequence that comprises a sequence that is at least 80%, 85%, 90%, 95%, 98% or 99% identical to SEQ ID NO: 15, a CDRH2 amino acid sequence that comprises a sequence that is at least 80%, 85%, 90%, 95%, 98% or 99% identical to SEQ ID NO: 16, and a CDRH3 amino acid sequence that comprises a sequence that is at least 80%, 85%, 90%, 95%, 98% or 99% identical to SEQ ID NO: 17, and a light chain variable region (VL) comprising a light chain complementarity determining region (CDRL) having a CDRL1 amino acid that comprises a sequence that is at least 80%, 85%, 90%, 95%, 98% or 99% identical to SEQ ID NO: 18, a CDRL2 amino acid sequence that comprises a sequence that is at least 80%, 85%, 90%, 95%, 98% or 99% identical to SEQ ID NO: 19, and a CDRHL 3 amino acid sequence that comprises a sequence that is at least 80%, 85%, 90%, 95%, 98% or 99% identical to SEQ ID NO: 20.

In an embodiment of the invention, the combination for use provides the gp120 binding protein comprises a VH comprising a heavy chain complementarity determining region (CDRH) having the CDRH1 amino acid sequence shown in in SEQ ID NO: 15, the CDRH2 amino acid sequence shown in in SEQ ID NO: 16, and the CDRH3 amino acid sequence shown in in SEQ ID NO: 17, and a VL comprising a light chain complementarity determining region (CDRL) having the CDRL1 amino acid sequence shown in in SEQ ID NO: 18, the CDRHL amino acid sequence shown in in SEQ ID NO: 19, and the CDRHL 3 amino acid sequence shown in in SEQ ID NO: 20.

In an embodiment of the invention, the combination for use provides the gp120 binding protein comprises a variable heavy chain region amino acid sequence that comprises a sequence that is at least 80%, 85%, 90%, 95%, 98%, or 99% identical to SEQ ID NO: 1. In an embodiment of the invention, the combination for use provides the gp120 binding protein comprises a variable heavy chain region amino acid sequence as shown in SEQ ID NO: 1.

In an embodiment of the invention, the combination for use provides the gp120 binding protein comprises a variable light chain region amino acid sequence that comprises a sequence that is at least 80%, 85%, 90%, 95%, 98%, or 99% identical to SEQ ID NO: 2. In an embodiment of the invention, the combination for use provides the gp120 binding protein comprises a variable light chain region amino acid sequence shown in SEQ ID NO: 2.

In an embodiment of the invention, the combination for use provides the gp120 binding protein comprises an antigen binding fragment. In an embodiment of the invention, the combination for use provides the antigen binding is a Fv, Fab, $F(ab')_2$, scFV or a $scFV_2$ fragment.

In an embodiment of the invention, the combination for use provides the monoclonal antibody comprises a recombinant constant domain comprising a modification that increases binding to a neonatal Fc receptor relative to an unmodified constant domain, wherein the recombinant domain is an IgG1 constant domain comprising M428L and N434S mutations.

In an embodiment of the invention, the combination for use provides the combination is co-administrated sequentially. In an embodiment of the invention, the combination for use provides the combination is co-administrated simultaneously. In an embodiment of the invention, the combination for use provides the combination is co-administrated parenterally.

In an embodiment of the invention, the combination for use provides the combination is co-administrated to the human once every month, once every 2 months, once every 3 months, or once every 6 months.

According to a further aspect of the invention, the invention provides use of cabotegravir or a pharmaceutically acceptable salt thereof and a gp120 binding protein as defined herein, in the manufacture or a medicament for use in the treatment of HIV.

According to a further aspect of the invention, the present invention provides a kit, wherein the kit comprises cabotegravir or a pharmaceutically acceptable salt thereof and a gp120 binding protein. In one embodiment, the kit comprises an integrase strand transfer inhibitor as disclosed herein and a gp120 binding protein as described herein. In one embodiment the kit comprises cabotegravir or a pharmaceutically acceptable salt thereof and a gp120 binding protein comprises a VH comprising a heavy chain complementarity determining region (CDRH) having the CDRH1 amino acid sequence shown in in SEQ ID NO: 15, the CDRH2 amino acid sequence shown in in SEQ ID NO: 16, and the CDRH3 amino acid sequence shown in in SEQ ID NO: 17, and a VL comprising a light chain complementarity determining region (CDRL) having the CDRL1 amino acid sequence shown in in SEQ ID NO: 18, the CDRHL amino acid sequence shown in in SEQ ID NO: 19, and the CDRHL 3 amino acid sequence shown in in SEQ ID NO: 20. In one embodiment the kit comprises cabotegravir or a pharmaceutically acceptable salt thereof and a gp120 binding protein comprises a VH comprising a heavy chain complementarity determining region (CDRH) having the CDRH1 amino acid sequence shown in in SEQ ID NO: 15, the CDRH2 amino acid sequence shown in in SEQ ID NO: 16, and the CDRH3 amino acid sequence shown in in SEQ ID NO: 17, and a VL comprising a light chain complementarity determining region (CDRL) having the CDRL1 amino acid sequence shown in in SEQ ID NO: 18, the CDRHL amino acid sequence shown in in SEQ ID NO: 19, and the CDRHL 3 amino acid sequence shown in in SEQ ID NO: 20, and an IgG1 constant domain comprising M428L and N434S mutations. In one embodiment, the kit comprises a syringe comprising the pharmaceutical composition of the invention as well as a leaflet comprising use instructions.

While not wishing to be bound by theory, it is thought that administering cabotegravir or a pharmaceutically acceptable salt thereof and a gp120 binding protein will target and disrupt two different parts of the HIV life cycle. In addition, it is believed that administering a compound with a high genetic barrier to resistance, the cabotegravir, with a compound with a low genetic barrier to resistance, the gp120 binding molecule, will reduce loss of therapeutic activity resulting from viral genetic code mutations.

The following non-limiting Examples illustrate the present invention.

EXAMPLES

Example 1: Preparation of Cabotegravir

TABLE 3

Composition of cabotegravir Injectable Suspension

| Component | Quantity (mg/mL) | Function |
|---|---|---|
| Cabotegravir | 200.0 | Active |
| Mannitol | 45.0 | Tonicity agent |
| Polysorbate 20 | 20.0 | Wetting agent |
| Polyethylene Glycol 3350 | 20.0 | Stabilizer |
| Water for Injection | QS to 1.0 mL | Solvent |

Cabotegravir, mannitol, polysorbate 20, PEG 3350, and water for injection were compounded and milled using a wet bead mill. The resulting suspension was filled into 3 mL, USP Type I glass vials at a fill volume of 1.5 mL, the vials are stoppered and sealed.

Example 2: 2-Drug Combination

Anti-HIV Evaluation of N6LS in 2-Drug Combination Drug Preparation

Provided below is an evaluation of the anti-HIV-1 activity and cytotoxicity of N6LS in two drug combination studies with Cabotegravir. N6LS was produced using standard methods described in the art. Stock solutions were prepared as listed in Table 4 and were thawed at room temperature on each day of assay setup to generate fresh working drug dilutions that were used that day in the assays. Working dilutions were not stored for re-use in subsequent experiments performed on different days. For each combination assay, N6LS was evaluated using a 20 nM high-test concentration with seven additional serial half-log dilutions. Each dilution of N6LS was tested in combination with five dilutions of the anti-HIV drug, Cabotegravir. In all cases the final DMSO concentration was <0.25%, which has been previously shown to have no effect in the described assays.

TABLE 4

Compound Solubilization Information

| Compound ID | Amount (mg) | Molecular Weight | DMSO Volume (μL) | Stock Concentration (mM) |
|---|---|---|---|---|
| N6LS | 5 | 150000 | 48 | 104 mg/ml (0.693 mM) |
| Cabotegravir | 6.9 | 405.35 | 1,702.2 | 10 |

Efficacy Evaluation in MT-4 Cells

For cell preparation, MT-4 cells (obtained from the NIH AIDS Research and Reference Reagent Program) were passaged in T-75 flasks prior to use in the antiviral assay. On the day preceding the assay, the cells were split 1:2 to assure they were in an exponential growth phase at the time of infection. Total cell and viability quantification were performed using a hemacytometer and trypan blue exclusion.

Cell viability needed to be greater than 95% for the cells to be utilized in the assay. The cells were re-suspended in tissue culture medium and added to the drug-containing microtiter plates in a volume of 110 μL and at a seeding density of 5.0×103 cells/well.

For virus preparation, the virus used for these tests was the CXCR4-tropic virus strain HIV-$1_{NL4-3}$. This virus was obtained from the NIH AIDS Research and Reference Reagent Program and was grown in MT-4 cells for the production of stock virus pools. For each assay, a pre-titered aliquot of virus was removed from the freezer (−80° C.) and allowed to thaw slowly to room temperature in a biological safety cabinet. The virus was re-suspended and diluted into tissue culture medium such that the amount of virus added to each well, in a volume of 50 μL, was the amount determined to give between 85 to 95% cell-killing at 6 days post infection. $TCID_{50}$ calculations by endpoint titration in MT-4 cells indicated that the multiplicity of infection of these assays was approximately 0.01.

For Plate Format, a checkerboard plate format was used to test five concentrations of Cabotegravir with eight concentrations of N6LS. Combination antiviral efficacy was evaluated on three identical assay plates (i.e., triplicate measurements) that included cell control wells (cells only) and virus control wells (cells plus virus). Combination cytotoxicity was evaluated in parallel on two identical assay plates (i.e., duplicate measurements) that included cell control wells. Antiviral efficacy and cellular toxicity were monitored by MTS staining at the experimental endpoint.

For MTS Endpoint for cell viability, at assay termination, the soluble tetrazolium-based dye MTS (CellTiter 96 Reagent, Promega) was added to each well to determine cell viability and quantify compound toxicity. MTS is metabolized by the mitochondria enzymes of metabolically active cells to yield a soluble formazan product, allowing the rapid quantitative analysis of cell viability and compound cytotoxicity. The reagent is a stable, single solution that does not require preparation before use. At termination of the assay, 20 μL of MTS reagent was added per well and the microtiter plates were then incubated for 3-4 hours at 37° C., 5% $CO_2$ for the HIV cytoprotection assay; the incubation intervals were chosen based on empirically determined times for optimal MTS reduction. Adhesive plate sealers were used in place of the lids, the sealed plates were inverted several times to mix the soluble formazan product and the plates were read spectrophotometrically at 490/650 nm with a Molecular Devices SpectraMax i3 plate reader.

Data Analysis

Combination antiviral assays were performed with MT-4 cells utilizing HIV-$1_{NL4-3}$, as described above. For each combination assay, five concentrations of Cabotegravir were tested with eight concentrations of N6LS. Three replicates were used to determine combination antiviral efficacy, and two replicates were used to determine combination cytotoxicity in uninfected MT-4. Each combination assay was performed three times.

The drug combination assay data was then analysed according to the method of Prichard and Shipman (Antiviral Research 14:181-206 [1990]) using the MacSynergy II program for data analysis and statistical evaluation. Briefly, the MacSynergy II program calculates the theoretical additive interactions of the drugs based on the Bliss Independence mathematical definition of expected effects for drug-drug interactions. The Bliss Independence model is based on statistical probability and assumes that the drugs act independently to affect virus replication; this Independent Effects model is also referred to as a Dual-Site (DS) model and is used for all combination analyses reported herein.

Theoretical additive interactions were calculated from the dose response curves for each drug used individually. This calculated additive surface, which represents predicted or additive interactions, was then subtracted from the experimentally determined dose-response surface to reveal regions of non-additive activity. The resulting surface would appear as a horizontal plane at 0% inhibition above calculated if the interactions were merely additive. Any peaks above this plane-of-additivity would be indicative of synergy. Similarly, any depressions below the plane-of-additivity would indicate antagonism. The 95% confidence intervals around the experimental dose-response surface were used to evaluate the data statistically and the volume of the peaks/depressions was calculated and used to quantify the volume of synergy/antagonism produced. The volume of the peaks observed in the synergy plots (in units of concentration times percent; e.g. $\mu M^2$%, $nM^2$%, nMμM %, etc.) was calculated by the program. This peak volume is the three-dimensional counterpart of the area under a 3-dimensional dose-response surface and is a quantitative measure of synergy or antagonism. For these studies, synergy is defined as drug combination yielding synergy volumes greater than 50. Slightly synergistic activity and highly synergistic activity have been operationally defined as yielding synergy volumes of 50-100 and >100, respectively. Additive drug interactions have synergy volumes in the range of −50 to 50, while synergy volumes between −50 and −100 are considered slightly antagonistic and those <−100 are highly antagonistic.

Results

Table 5 summarizes the results from the antiviral testing of N6LS against HIV-$1_{NL4-3}$ in MT-4. As summarized in Table 5 the combination of N6LS with the Cabotegravir for this study resulted in mainly synergistic or additive interactions.

TABLE 5

Antiviral Efficacy Results of N6LS in Combination with Cabotegravir in MT-4 Cells (95% Confidence Values)

| Compound[1] | Synergy/Antagonism Volume ($nM^2$ %)[1] Result 1 | Result 2 | Result 3 | Mean Synergy/Antagonism Volume ($nM^2$; n = 3)[2] |
|---|---|---|---|---|
| Integrase strand transfer inhibitor | | | | |
| Cabotegravir | 2.32/−45.27 | 187.5/0 | 61.7/−39.56 | 83.84/−28.28 |

[1]The MacSynergy II program takes the raw data from individual experiments and calculates a positive (synergy) or negative (antagonism) value for each drug-drug combination [these values can be found in the Antiviral Synergy Plot (95%) sections of the spreadsheets found in Appendices II-IX]. Positive values are summed to give a Volume of Synergy and negative values are summed to give a Volume of Antagonism (both values are reported for each experiment).

[2]The Antiviral Synergy Plot (95%) datasets from multiple experiments (n = 3) are combined and arithmetic means are calculated for each drug-drug concentration. The positive and negative values are individually summed to respectively give Mean Volumes for synergistic and antagonistic interactions.

SEQUENCE LISTINGS

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

TABLE 6

| N6 Sequence Listings | | |
|---|---|---|
| SEQ ID NO: 1 | RAHLVQSGTAMKKPGASVRVSCQTSGYTFTAHIL FWFRQAPGRGLEWVGWIKPQYGAVNFGGGFRDR VTLTRDVYREIAYMDIRGLKPDDTAVYYCARDRSY GDSSWALDAWGQGTTVVVSA | an amino acid sequence of the VH of the N6 mAb |
| SEQ ID NO: 2 | YIHVTQSPSSLSVSIGDRVTINCQTSQGVGSDLH WYQHKPGRAPKLLIHHTSSVEDGVPSRFSGSGFH TSFNLTISDLQADDIATYYCQVLQFFGRGSRLHIK | an amino acid sequence of the VL of the N6 mAb |
| SEQ ID NO: 3 | CGAGCGCACCTGGTACAATCAGGGACTGCGATG AAGAAACCGGGGGCCTCAGTAAGAGTCTCCTGC CAGACCTCTGGATACACCTTTACCGCCCACATAT TATTTTGGTTCCGACAGGCCCCCGGGCGAGGAC TTGAGTGGGTGGGGTGGATCAAGCCACAATATG GGGCCGTGAATTTTGGTGGTGGTTTTCGGGACA GGGTCACATTGACTCGAGACGTATATAGAGAGA TTGCGTACATGGACATCAGAGGCCTTAAACCTGA CGACACGGCCGTCTATTACTGTGCGAGAGACCG TTCCTATGGCGACTCCTCTTGGGCCTTAGATGCC TGGGGACAGGGAACGACGGTCGTCGTCTCCGCG | a nucleic acid sequence encoding the VH of the N6 mAb |
| SEQ ID NO: 4 | TACATCCACGTGACCCAGTCTCCGTCCTCCCTGT CTGTGTCTATTGGAGACAGAGTCACCATCAATTG CCAGACGAGTCAGGGTGTTGGCAGTGACCTACA TTGGTATCAACACAAACCGGGGAGAGCCCCTAA ACTCTTGATCCACCATACCTCTTCTGTGGAAGAC GGTGTCCCCTCAAGATTCAGCGGCTCTGGATTT CACACATCTTTTAATCTGACCATCAGCGACCTAC AGGCTGACGACATTGCCACATATTACTGTCAAGT TTTACAATTTTTCGGCCGAGGGAGTCGACTC CATATTAAA | a nucleic acid sequence encoding the VL of the N6 mAb |
| SEQ ID NO: 5 | RAHLVQSGTAMKKPGASVRVSCQTSGYTFTAHIL FWFRQAPGRGLEWVGWIKPQYGAVNFGGGFRDR VTLTRDVYREIAYMDIRGLKPDDTAVYYCARDRSY GDSSWALDAWGQGTTVVVSAASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTCPPCPAPELL GGPSVFLFPPKPKDTLMISRTPEVTCVVVDVSHED PEVKFNWYVDGVEVHNAKTKPREEQYNSTYRVVS VLTVLHQDWLNGKEYKCKVSNKALPAPIEKTISKA KGQPREPQVYTLPPSRDELTKNQVSLTCLVKGFYP SDIAVEWESNGQPENNYKTTPPVLDSDGSFFLYSK LTVDKSRWQQGNVFSCSVMHEALHNHYTQKSLS LSPGK | a heavy chain sequence including the N6 VH |
| SEQ ID NO: 6 | CGAGCGCACCTGGTACAATCAGGGACTGCGATG AAGAAACCGGGGGCCTCAGTAAGAGTCTCCTGC CAGACCTCTGGATACACCTTTACCGCCCACATAT TATTTTGGTTCCGACAGGCCCCCGGGCGAGGAC TTGAGTGGGTGGGGTGGATCAAGCCACAATATG GGGCCGTGAATTTTGGTGGTGGTTTTCGGGACA GGGTCACATTGACTCGAGACGTATATAGAGAGA TTGCGTACATGGACATCAGAGGCCTTAAACCTGA CGACACGGCCGTCTATTACTGTGCGAGAGACCG TTCCTATGGCGACTCCTCTTGGGCCTTAGATGCC TGGGGACAGGGAACGACGGTCGTCGTCTCCGCG GCGTCGACCAAGGGCCCATCGGTCTTCCCCCTG GCACCCTCCTCCAAGAGCACCTCTGGGGGCACA GCGGCCCTGGGCTGCCTGGTCAAGGACTACTTC CCCGAACCGGTGACGGTGTCGTGGAACTCAGGC GCCCTGACCAGCGGCGTGCACACCTTCCCGGCT GTCCTACAGTCCTCAGGACTCTACTCCCTCAGCA GCGTGGTGACCGTGCCCTCCAGCAGCTTGGGCA CCCAGACCTACATCTGCAACGTGAATCACAAGCC CAGCAACACCAAGGTGGACAAGAAAGTTGAGCC CAAATCTTGTGACAAAACTCACACATGCCCACCG TGCCCAGCACCTGAACTCCTGGGGGGACCGTCA GTCTTCCTCTTCCCCCCAAAACCCAAGGACACCC TCATGATCTCCCGGACCCCTGAGGTCACATGCGT GGTGGTGGACGTGAGCCACGAAGACCCTGAGGT CAAGTTCAACTGGTACGTGGACGGCGTGGAGGT GCATAATGCCAAGACAAAGCCGCGGGAGGAGCA GTACAACAGCACGTACCGTGTGGTCAGCGTCCT CACCGTCCTGCACCAGGACTGGCTGAATGGCAA GGAGTACAAGTGCAAGGTCTCCAACAAAGCCCT CCCAGCCCCCATCGAGAAAACCATCTCCAAAGCC | a nucleic acid sequence encoding a heavy chain including the N6 VH |

TABLE 6-continued

| N6 Sequence Listings | | |
|---|---|---|
| | AAAGGGCAGCCCCGAGAACCACAGGTGTACACC<br>CTGCCCCCATCCCGGGATGAGCTGACCAAGAAC<br>CAGGTCAGCCTGACCTGCCTGGTCAAAGGCTTC<br>TATCCCAGCGACATCGCCGTGGAGTGGGAGAGC<br>AATGGGCAGCCGGAGAACAACTACAAGACCACG<br>CCTCCCGTGCTGGACTCCGACGGCTCCTTCTTCC<br>TCTACAGCAAGCTCACCGTGGACAAGAGCAGGT<br>GGCAGCAGGGGAACGTCTTCTCATGCTCCGTGA<br>TGCATGAGGCTCTGCACAACCACTACACGCAGAA<br>GAGCCTCTCCCTGTCTCCG GGTAAA | |
| SEQ ID NO: 7 | YIHVTQSPSSLSVSIGDRVTINCQTSQGVGSDLH<br>WYQHKPGRAPKLLIHHTSSVEDGVPSRFSGSGFH<br>TSFNLTISDLQADDIATYYCQVLQFFGRGSRLHIK<br>RTVAAPSVFIFPPSDEQLKSGTASVVCLLNNFYPRE<br>AKVQWKVDNALQSGNSQESVTEQDSKDSTYSLS<br>STLTLSKADYEKHKVYACEVTHQGLSSP<br>VTKSFNRGEC | a light chain sequence including the N6 VL |
| SEQ ID NO: 8 | TACATCCACGTGACCCAGTCTCCGTCCTCCCTGT<br>CTGTGTCTATTGGAGACAGAGTCACCATCAATTG<br>CCAGACGAGTCAGGGTGTTGGCAGTGACCTACA<br>TTGGTATCAACACAAACCGGGGAGAGCCCCTAA<br>ACTCTTGATCCACCATACCTCTTCTGTGGAAGAC<br>GGTGTCCCCTCAAGATTCAGCGGCTCTGGATTT<br>CACACATCTTTTAATCTGACCATCAGCGACCTAC<br>AGGCTGACGACATTGCCACATATTACTGTCAAGT<br>TTTACAATTTTTCGGCCGAGGGAGTCGACTCCAT<br>ATTAAACGTACGGTGGCTGCACCATCTGTCTTCA<br>TCTTCCCGCCATCTGATGAGCAGTTGAAATCTGG<br>AACTGCCTCTGTTGTGTGCCTGCTGAATAACTTC<br>TACCCCAGAGAAGCCAAAGTGCAGTGGAAGGTG<br>GACAACGCCCTGCAGAGCGGAAACAGCCAGGAA<br>AGCGTGACAGAGCAGGATTCCAAGGATTCCACA<br>TACAGCCTGAGCAGCACACTGACACTGTCCAAG<br>GCCGACTACGAGAAGCACAAGGTGTACGCCTGC<br>GAAGTGACACACCAGGGACTGTCCTCCCCTGTG<br>ACAAAGAGCTTCAACAGAGGAGAATGC | a nucleic acid sequence encoding a light chain including the N6 VH |
| SEQ ID NO: 9 | RAHLVQSGTAMKKPGASVRVSCQTSGYTFTAHIL<br>FWFRQAPGRGLEWVGWIKPQYGAVNFGGGFRDR<br>VTLTRDVYREIAYMDIRGLKPDDTAVYYCARDRSY<br>GDSSWALDAWGQGTTVVVSAASTKGPSVFPLAPS<br>SKSTSGGTAALGCLVKDYFPEPVTVSWNSGALTS<br>GVHTFPAVLQSSGLYSLSSVVTVPSSSLGTQTYIC<br>NVNHKPSNTKVDKRVEPKSCDKTHTCPPCPAPELL<br>GGPSVFLFPPKPKDTLMISRTPEVTCVVVDVSHED<br>PEVKFNWYVDGVEVHNAKTKPREEQYNSTYRVVS<br>VLTVLHQDWLNGEEYKCKVSNKALPAPIEKTISKA<br>KGQPREPQVYTLPPSREEMTKNQVSLTCLVKGFYP<br>SDIAVEWESNGQPENNYKTTPPVLDSDGSFFLYSK<br>LTVDKSRWQQGNVFSCSVMHEALHNHYTQKSLS<br>LSP GK | a heavy chain sequence including the N6 VH as isolated from a human donor, which includes polymorphisms compared to SEQ ID NO: 5 |
| SEQ ID NO: 10 | CGAGCGCACCTGGTACAATCAGGGACTGCGATG<br>AAGAAACCGGGGGCCTCAGTAAGAGTCTCCTGC<br>CAGACCTCTGGATACACCTTTACCGCCCACATAT<br>TATTTTGGTTCCGACAGGCCCCCGGGCGAGGAC<br>TTGAGTGGGTGGGGTGGATCAAGCCACAATATG<br>GGGCCGTGAATTTTGGTGGTGGTTTTCGGGACA<br>GGGTCACATTGACTCGAGACGTATATAGAGAGA<br>TTGCGTACATGGACATCAGAGGCCTTAAACCTGA<br>CGACACGGCCGTCTATTACTGTGCGAGAGACCG<br>TTCCTATGGCGACTCCTCTTGGGCCTTAGATGCC<br>TGGGGACAGGGAACGACGGTCGTCGTCTCCGCG<br>GCCTCCACCAAGGGCCCATCGGTCTTCCCCCTG<br>GCACCCTCCTCCAAGAGCACCTCTGGGGGCACA<br>GCGGCCCTGGGCTGCCTGGTCAAGGACTACTTC<br>CCCGAACCGGTGACGGTGTCGTGGAACTCAGGC<br>GCCCTGACCAGCGGCGTGCACACCTTCCCGGCT<br>GTCCTACAGTCCTCAGGACTCTACTCCCTCAGCA<br>GCGTGGTGACCGTGCCCTCCAGCAGCTTGGGCA<br>CCCAGACCTACATCTGCAACGTGAATCACAAGCC<br>CAGCAACACCAAGGTGGACAAGAGAGTTGAGCC<br>CAAATCTTGTGACAAAACTCACACATGCCCACCG<br>TGCCCAGCACCTGAACTCCTGGGGGGACCGTCA<br>GTCTTCCTCTTCCCCCCAAAACCCAAGGACACCC<br>TCATGATCTCCCGGACCCCTGAGGTCACATGCGT | a sequence of the nucleic acid molecule encoding the N6 VH as isolated from a human donor |

TABLE 6-continued

| N6 Sequence Listings | | |
|---|---|---|
| | GGTGGTGGACGTGAGCCACGAAGACCCTGAGGT CAAGTTCAACTGGTACGTGGACGGCGTGGAGGT GCATAATGCCAAGACAAAGCCGCGGGAGGAGCA GTACAACAGCACGTACCGTGTGGTCAGCGTCCT CACCGTCCTGCACCAGGACTGGCTGAATGGCGA GGAGTACAAGTGCAAGGTCTCCAACAAAGCCCT CCCAGCCCCCATCGAGAAAACCATCTCCAAAGCC AAAGGGCAGCCCCGAGAACCACAGGTGTACACC CTGCCCCCATCCCGGGAGGAGATGACCAAGAAC CAGGTCAGCCTGACCTGCCTTGTCAAAGGCTTCT ATCCCAGCGACATCGCCGTGGAGTGGGAGAGCA ATGGGCAGCCGGAGAACAACTACAAGACCACGC CTCCCGTGCTGGACTCCGACGGCTCCTTCTTCCT CTACAGCAAGCTCACCGTGGACAAGAGCAGGTG GCAGCAGGGGAACGTCTTCTCATGCTCCGTGAT GCATGAGGCTCTGCACAACCACTACACGCAGAA GAGCCTCTCCCTGTCTCCG GGTAAA | |
| SEQ ID NO: 11 | CGAGGGCACTTGGTGCAGTCAGGGACTGAGGTG AAGAAACCGGGGGCCTCAGTGAGAGTCTCCTGC GAGACTTCTGGATACACCTTCACCGCCTACATTT TACATTGGTTCCGACAGGCCCCCGGACGAGGGC TTGAGTGGATGGGGTGGATCAAGCCAAAATATG GAGCCGTCAATTATGCTCATGCATTTCAGGGCA GGGTCACCCTGACCAGAGACATATATAGAGACA CTGCATACATGGACTTGAGTGGCCTAAGATTCG ACGACACGGCCGTCTATTACTGTGCGAGAGATC GCGTTTATGACGATTCGTCTTGGCAATTGGATCC CTGGGGCCAGGGAACTTCGGTCATCGTCTCCTC A | a nucleotide sequence encoding the N6 I1 VH intermediate |
| SEQ ID NO: 12 | CGAGGGCACTTGGTGCAGTCAGGGACTGAGGTG AAGAAACCGGGGGCCTCAGTGAGAGTCTCCTGC GAGACTTCTGGATACACCTTCACCGCCCACATTT TACATTGGTTCCGACAGGCCCCCGGACGAGGGC TTGAGTGGATGGGGTGGATCAAGCCAAAATATG GAGCCGTCAATTATGCTCATGCATTTCAGGGCA GGGTCACCCTGACCAGAGACATATATAGAGACA CTGCATACATGGACTTGAGTGGCCTAAGATTCG ACGACACGGCCGTCTATTACTGTGCGAGAGATC GCGTTTATGACGATTCGTCTTGGCAATTGGATCC CTGGGGCCAGGGAACTTCGGTCATCGTCTCCTC A | a nucleotide sequence encoding the N6 I2 VH intermediate |
| SEQ ID NO: 13 | CGAGCGCACTTGGTGCAGTCAGGGACTGCGGTG AAGAAACCGGGGGCCTCAGTGAGAGTCTCCTGC GAGACTTCTGGATACACCTTCACCGCCCACATTT TATATTGGTTCCGACAGGCCCCCGGACGAGGGC TTGAGTGGGTGGGGTGGATCAAGCCACAATATG GGGCCGTGAATTTTGGTGGTGGTTTTCGGGGCA GGGTCACCCTGACCAGAGACATATATAGAGACA CTGCATACATGGACATCAGTGGCCTAAGATTCGA CGACACGGCCGTCTATTACTGTGCGAGAGATCG CTCCTATGACGACTCCTCTTGGGCCTTAGATGCC TGGGGACAGGGAACGACGGTCGTCGTCTCCGCG | a nucleotide sequence encoding the N6 I3 VH intermediate |
| SEQ ID NO: 14 | CGAGCGCACCTGGTACAATCAGGGACTGCGATG AAGAAACCGGGGGCCTCAGTAAGAGTCTCCTGC CAGACCTCTGGATACACCTTTACCGCCCACATAT TATTTTGGTTCCGACAGGCCCCCGGGCGAGGAC TTGAGTGGGTGGGGTGGATCAAGCCACAATATG GGGCCGTGAATTTTGGTGGTGGTTTTCGGGACA GGGTCACATTGACTCGAGACATATATAGAGAGA TTGCGTACATGGACATCAGAGGCCTTAAACTTGA CGACACGGCCGTCTATTACTGTGCGAGAGACCG TTCCTATGGCGACTCCTCTTGGGCCTTAGATGCC TGGGGACAGGGAACGACGGTCGTCGTCTCCGCG | a nucleotide sequence encoding the N6 I4 VH intermediate |
| SEQ ID NO: 15 | AHILF | an amino acid sequence of N6 CDRH1 |
| SEQ ID NO: 16 | WIKPQYGAVNFGGGFRD | an amino acid sequence of N6 CDRH2 |

TABLE 6-continued

| N6 Sequence Listings | | |
|---|---|---|
| SEQ ID NO: 17 | DRSYGDSSWALDA | an amino acid sequence of N6 CDRH3 |
| SEQ ID NO: 18 | QTSQGVGSDLH | an amino acid sequence of N6 CDRL1 |
| SEQ ID NO: 19 | HTSSVED | an amino acid sequence of N6 CDRL2 |
| SEQ ID NO: 20 | QVLQF | an amino acid sequence of N6 CDRL3 |
| SEQ ID NO: 21 | MGWSCIILFLVATATGVHSRAHLVQSGTAMKKPG ASVRVSCQTSGYTFTAHILFWFRQAPGRGLEWVG WIKPQYGAVNFGGGFRDRVTLTRDVYREIAYMDI RGLKPDDTAVYYCARDRSYGDSSWALDAWGQGT TVVVSAASTKGPSVFPLAPSSKSTSGGTAALGCLV KDYFPEPVTVSWNSGALTSGVHTFPAVLQSSGLYS LSSVVTVPSSSLGTQTYICNVNHKPSNTKVDKKVE PKSCDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKEY KCKVSNKALPAPIEKTISKAKGQPREPQVYTLPPSR DELTKNQVSLTCLVKGFYPSDIAVEWESNGQPEN NYKTTPPVLDSDGSFFLYSKLTVDKSRWQQGNVF SCSVLHEALHSHYTQKSLSLSPGK | an amino acid sequence of the N6-LS heavy chain |
| SEQ ID NO: 22 | MGWSCIILFLVATATGVHSYIHVTQSPSSLSVSIG DRVTINCQTSQGVGSDLHWYQHKPGRAPKLLIHH TSSVEDGVPSRFSGSGFHTSFNLTISDLQADDIAT YYCQVLQFFGRGSRLHIKRTVAAPSVFIFPPSDEQL KSGTASVVCLLNNFYPREAKVQWKVDNALQSGNS QESVTEQDSKDSTYSLSSTLTLSKADYEKHKVYAC EVTHQGLSSPVTKSFNRGEC | an amino acid sequence of the N6-LS light chain |

The invention claimed is:

1. A method of treating an HIV infection in a human in need thereof comprising:

administering to a human a therapeutically effective amount of cabotegravir or a pharmaceutically acceptable salt thereof and a therapeutically effective amount of an HIV gp120 binding protein or an antigen binding fragment thereof, wherein the gp120 binding protein comprises an isolated monoclonal antibody which comprises:

a heavy chain variable region ($V_H$) comprising a heavy chain complementarity determining region (HCDR) 1, a HCDR2, and a HCDR3 set forth as SEQ ID NOs: 15, 16, and 17, respectively; and a light chain variable region ($V_L$) comprising a light chain complementarity determining region (LCDR) 1, a LCDR2, and a LCDR3 set forth as SEQ ID NOs: 18, 19, and 20, respectively.

wherein the $V_H$ comprises an amino acid sequence that is at least 80%, 85%, 90%, 95%, 98%, or 99% identical to SEQ ID NO: 1 and the $V_L$ comprises an amino acid sequence that is at least 80%, 85%, 90%, 95%, 98%, or 99% identical to SEQ ID NO: 2.

2. The method according to claim 1, wherein the HIV gp120 binding protein neutralizes HIV-1.

3. The method according to claim 1, wherein the HIV gp120 binding protein comprises a recombinant constant domain comprising one or more amino acid modifications that increase the half-life of the antibody.

4. The method according to claim 1, wherein the $V_H$ comprises the amino acid sequence having at least 95% sequence identity to SEQ ID NO: 1.

5. The method according to claim 1, wherein the $V_H$ comprises the amino acid sequence of SEQ ID NO: 1.

6. The method according to claim 1, wherein the $V_L$ comprises the amino acid sequence having at least 95% sequence identity to SEQ ID NO: 2.

7. The method according to claim 1, wherein the $V_L$ comprises the amino acid sequence of SEQ ID NO: 2.

8. The method according to claim 3, wherein the recombinant constant domain comprises one or more mutations from the group consisting of: M252Y/S254T/T256E, M428L/N434S, T250Q/M428L, V259I/V308F/M428L, E380A/N434A, T307A/E380A/N434A, and H433K/N434F.

9. The method according to claim 3, wherein the recombinant constant domain comprises M428L and N434S mutations.

10. The method according to claim 1, wherein the antibody is an IgG, IgA or IgM antibody.

11. The method according to claim 1, wherein the cabotegravir or the pharmaceutically acceptable salt thereof and the HIV gp120 binding protein are administered separately.

12. The method according to claim 1, the cabotegravir or the pharmaceutically acceptable salt thereof and the HIV gp120 binding protein are administered simultaneously.

13. The method according to claim 1, wherein the cabotegravir or the pharmaceutically acceptable salt thereof and the HIV gp120 binding protein are administered parenterally.

14. The method according to claim 1, wherein the cabotegravir or the pharmaceutically acceptable salt thereof and the HIV gp120 binding protein are administered once every month, once every 2 months, once every 3 months, or once every 6 months.

15. The method according to claim 1, wherein the $V_H$ comprises the amino acid sequence of SEQ ID NO: 1 and wherein the $V_L$ comprises the amino acid sequence of SEQ ID NO: 2.

* * * * *